(12) United States Patent
Tyber et al.

(10) Patent No.: US 10,639,163 B2
(45) Date of Patent: May 5, 2020

(54) SMALL JOINT FIXATION

(71) Applicant: Tyber Medical LLC, Bethlehem, PA (US)

(72) Inventors: Jeffrey Tyber, Breinigsville, PA (US); Rui Ferreira, Livingston, NJ (US); Christopher Faresich, Denville, NJ (US); Donald Buss, Macungie, PA (US)

(73) Assignee: Tyber Medical, LLC, Bethlehem, PA (US)

( * ) Notice: Subject to any disclaimer, the term of this patent is extended or adjusted under 35 U.S.C. 154(b) by 14 days.

(21) Appl. No.: 16/049,854

(22) Filed: Jul. 31, 2018

(65) Prior Publication Data

US 2018/0344471 A1 Dec. 6, 2018

Related U.S. Application Data

(60) Division of application No. 15/213,935, filed on Jul. 19, 2016, now Pat. No. 10,058,431, which is a
(Continued)

(51) Int. Cl.
*A61F 2/42* (2006.01)
*A61B 17/16* (2006.01)
(Continued)

(52) U.S. Cl.
CPC ........ *A61F 2/4225* (2013.01); *A61B 17/1615* (2013.01); *A61B 17/1682* (2013.01); *A61B 17/70* (2013.01); *A61B 17/7291* (2013.01); *A61B 17/8095* (2013.01); *A61B 17/8852* (2013.01); *A61B 90/94* (2016.02); *A61F 2/28* (2013.01); *A61F 2/44* (2013.01); *A61F 2/447* (2013.01); *A61F 2/4455* (2013.01); *A61F 2/4465* (2013.01); *A61F 2/4603* (2013.01);
(Continued)

(58) Field of Classification Search
CPC ......... A61F 2/42; A61F 2/4225; A61F 2/4241
See application file for complete search history.

(56) References Cited

U.S. PATENT DOCUMENTS 6,696,073 B2 * 2/2004 Boyce ................ A61B 17/0401
424/422
2005/0010215 A1 1/2005 Delecrin et al.
(Continued)

FOREIGN PATENT DOCUMENTS

FR 2808182 11/2001
WO WO2016/044053 3/2016

OTHER PUBLICATIONS

PCT/US2017/042496. International Preliminary Report on Patentability, dated Jan. 22, 2019.
(Continued)

*Primary Examiner* — Si Ming Ku
(74) *Attorney, Agent, or Firm* — Joseph E. Maenner; Maenner & Associates, LLC

(57) ABSTRACT

Disclosed is a medical device having a first implant portion having a proximal end, a second implant portion connected to the first implant portion, the second implant portion having a distal end, and a driver assembly removably connected to the distal end, the driver assembly comprising a drill connected to the distal end at a connection.

16 Claims, 28 Drawing Sheets

Related U.S. Application Data continuation-in-part of application No. 15/162,657, filed on May 24, 2016, now Pat. No. 10,369,251, which is a continuation-in-part of application No. 14/948,322, filed on Nov. 22, 2015, now Pat. No. 10,201,433, which is a continuation-in-part of application No. 14/513,300, filed on Oct. 14, 2014, which is a continuation-in-part of application No. 14/054,100, filed on Oct. 15, 2013, now Pat. No. 9,387,087.

(60) Provisional application No. 61/715,891, filed on Oct. 19, 2012.

(51) Int. Cl.

| | | |
|---|---|---|
| *A61B 17/72* | (2006.01) | |
| *A61B 17/80* | (2006.01) | |
| *A61B 17/88* | (2006.01) | |
| *A61B 90/94* | (2016.01) | |
| *A61F 2/28* | (2006.01) | |
| *A61F 2/44* | (2006.01) | |
| *A61F 2/46* | (2006.01) | |
| *A61L 27/02* | (2006.01) | |
| *A61L 27/04* | (2006.01) | |
| *A61L 27/30* | (2006.01) | |
| *A61B 17/70* | (2006.01) | |
| *A61F 2/30* | (2006.01) | |

(52) U.S. Cl.
CPC .......... *A61F 2/4606* (2013.01); *A61F 2/4611* (2013.01); *A61L 27/025* (2013.01); *A61L 27/04* (2013.01); *A61L 27/306* (2013.01); *A61B 17/7059* (2013.01); *A61F 2/30771* (2013.01); *A61F 2002/2817* (2013.01); *A61F 2002/2835* (2013.01); *A61F 2002/3008* (2013.01); *A61F 2002/30011* (2013.01); *A61F 2002/30028* (2013.01); *A61F 2002/3071* (2013.01); *A61F 2002/3082* (2013.01); *A61F 2002/3084* (2013.01); *A61F 2002/3092* (2013.01); *A61F 2002/3093* (2013.01); *A61F 2002/30266* (2013.01); *A61F 2002/30281* (2013.01); *A61F 2002/30321* (2013.01); *A61F 2002/30326* (2013.01); *A61F 2002/30355* (2013.01); *A61F 2002/30507* (2013.01); *A61F 2002/30515* (2013.01); *A61F 2002/30523* (2013.01); *A61F 2002/30538* (2013.01); *A61F 2002/30556* (2013.01); *A61F 2002/30578* (2013.01); *A61F 2002/30579* (2013.01); *A61F 2002/30593* (2013.01); *A61F 2002/30622* (2013.01); *A61F 2002/30774* (2013.01); *A61F 2002/30808* (2013.01); *A61F 2002/30836* (2013.01); *A61F 2002/30843* (2013.01); *A61F 2002/30904* (2013.01); *A61F 2002/4228* (2013.01); *A61F 2002/4627* (2013.01); *A61F 2220/0016* (2013.01); *A61F 2310/00407* (2013.01); *A61F 2310/00461* (2013.01); *A61F 2310/00796* (2013.01); *A61L 2400/18* (2013.01)

(56) References Cited

U.S. PATENT DOCUMENTS

| | | | |
|---|---|---|---|
| 2005/0216099 A1 | 9/2005 | O'Driscoll | |
| 2007/0202144 A1 | 8/2007 | Hellerbrand et al. | |
| 2008/0221681 A1* | 9/2008 | Trieu | A61L 27/32 623/11.11 |
| 2009/0036926 A1 | 2/2009 | Hestad et al. | |
| 2011/0144644 A1* | 6/2011 | Prandi | A61B 17/7233 606/62 |
| 2011/0301652 A1* | 12/2011 | Reed | A61B 17/7291 606/319 |
| 2013/0190831 A1 | 7/2013 | Ek | |
| 2013/0253585 A1 | 9/2013 | Garcia et al. | |
| 2014/0025123 A1 | 1/2014 | Zeetser | |
| 2014/0031935 A1 | 1/2014 | Donner et al. | |
| 2014/0114415 A1 | 4/2014 | Tyber | |
| 2014/0172028 A1 | 6/2014 | Meredith | |
| 2015/0012050 A1 | 1/2015 | Anderson | |
| 2015/0045903 A1* | 2/2015 | Neal | B23K 15/0006 623/21.18 |
| 2017/0065424 A1* | 3/2017 | Lauf | A61B 17/7291 |

OTHER PUBLICATIONS

PCT/US2017/042496, International Search Report and Written Opinion, dated Dec. 17, 2017. 12 pages.
Office Action for U.S. Appl. No. 15/213,935, dated Feb. 27, 2017.
Final Office Action for U.S. Appl. No. 15/213,935, dated Aug. 1, 2017.
EPO Search Report for EP 17831655.0 dated Feb. 27, 2020.

\* cited by examiner

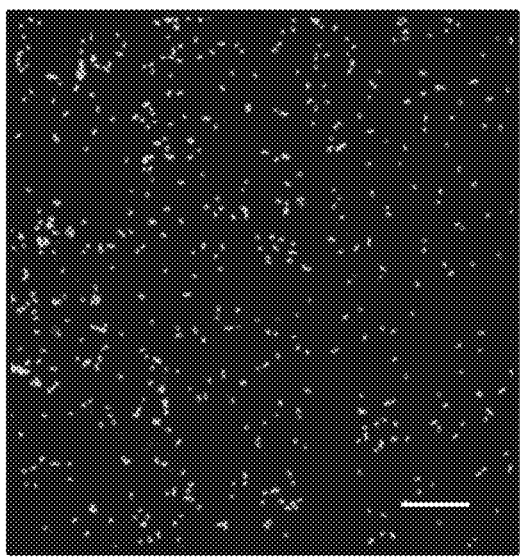 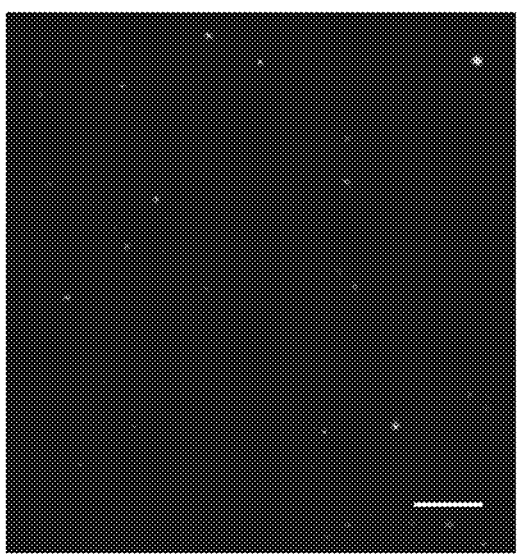
FIG. 23A　　　　　　　　　FIG. 23B
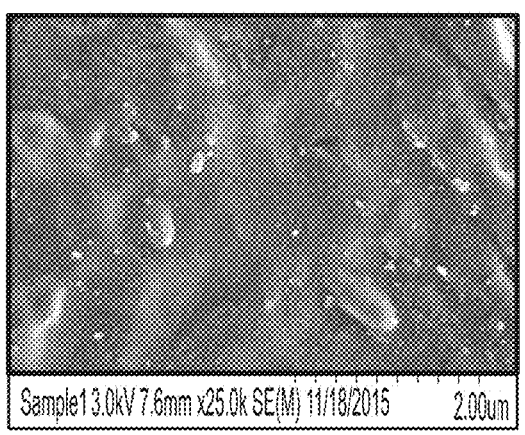 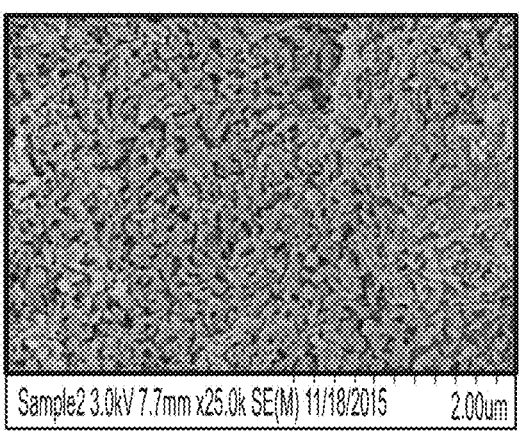
FIG. 23C　　　　　　　　　FIG. 23D Day 3 & 5 (Osteoblasts)

SMALL JOINT FIXATION

CROSS-REFERENCE TO RELATED APPLICATIONS

This a divisional application of U.S. patent application Ser. No. 15/213,935, filed on Jul. 19, 2016 (allowed), which is a continuation-in-part of co-pending application Ser. No. 15/162,657, filed on May 24, 2016, which is a continuation-in-part of application Ser. No. 14/948,322, filed on Nov. 22, 2015, which is a continuation-in-part of co-pending application Ser. No. 14/513,300, filed on Oct. 14, 2014, which is a continuation-in-part application of U.S. patent application Ser. No. 14/054,100, filed on Oct. 15, 2013, which claims priority from U.S. Provisional Patent Application Ser. No. 61/715,891, filed on Oct. 19, 2012, all of which are incorporated by reference herein in their entireties.

BACKGROUND OF THE INVENTION

Field of the Invention

The present invention relates to medical implants, and, in particular, to implants for the treatment of digital deformities, such as hammer toe.

Description of the Related Art

A digital deformity, such as hammer toe, is a deformity of the second, third or fourth digit. In this condition, the digit is bent at the middle joint, so that the digit resembles a hammer. Initially, digital deformities can be flexible and can be corrected with simple measures but if left untreated, they can become fixed and require surgery.

It would be beneficial to provide a surgical implant that can correct a digital deformity and provide small joint fusion.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a unitary construction medical device comprising a first implant portion having a proximal end, a second implant portion connected to the first implant portion, the second implant portion having a distal end, and a driver assembly removably connected to the distal end, the driver assembly comprising a drill connected to the distal end at a connection.

In another embodiment, the present invention is a method of joining adjacent bone structures comprising the steps of providing the medical device described above; inserting the driver assembly into a driver device; placing the first implant portion against a first bone structure; inserting the first implant portion into the first bone structure; separating the second implant portion from the driver assembly; forming an opening in a second bone structure, adjacent to the first bone structure; and inserting the second implant portion into the opening.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 23A shows an untreated titanium surface and bacterial growth thereon;

FIG. 23B shows the surface of FIG. 23A treated with $TiO_2$ after 16 hours of incubation;

FIG. 23C shows a Scanning Electron Microscope (SEM) image of the untreated titanium surface;

FIG. 23D shows an SEM image of the treated $TiO_2$ surface after 16 hours of incubation;

DETAILED DESCRIPTION

Figure 1:
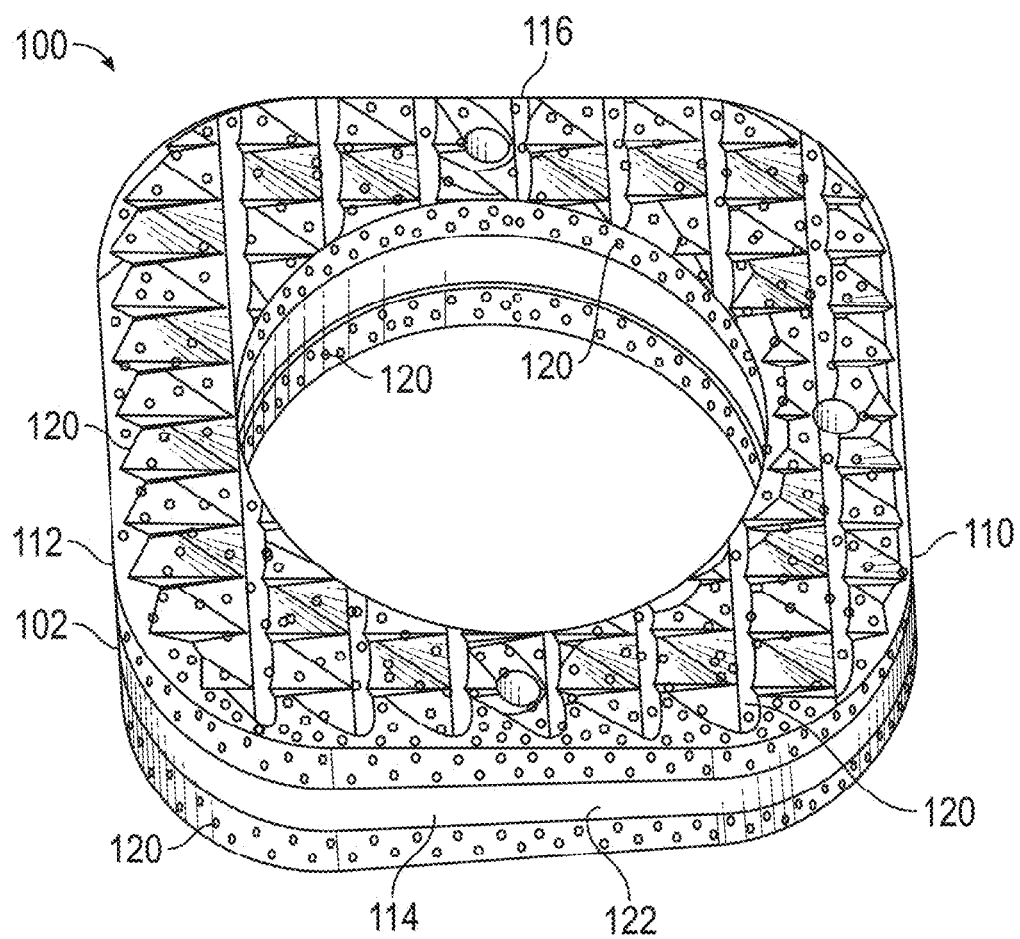
FIG. 1 shows a perspective view of a wedge implant according to a first exemplary embodiment of the present invention.

In the drawings, like numerals indicate like elements throughout. Certain terminology is used herein for convenience only and is not to be taken as a limitation on the present invention. For purposes of this description, the terms "anterior", "posterior", "lateral", "medial", "superior" and "inferior" describe the position of surfaces or features relative to the anatomy. The term "anterior" refers to features having a relative position toward the front side of a spine, and "posterior" refers to features having a relative position toward the rear side of the spine. The term "lateral" refers to features having a relative position toward the left or right side of the spine. The term "medial" refers to features having a relative position toward the center of the spine. The term "cranial" refers to features having a relative position above other features, and the term "caudal" refers to features having a relative position below other features. The terminology includes the words specifically mentioned, derivatives thereof and words of similar import.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Referring to FIGS. 1-6, a wedge implant 100 according to a first exemplary embodiment of the present invention is shown. Wedge implant 100 is inserted into a single vertebra 50 in a spine 52 to readjust the caudal and cranial plans of vertebra 50 to alleviate scoliosis in spine 52. While a single wedge implant 100 is shown being inserted into a single vertebra 50, those skilled in the art will recognize that additional wedge implants 100 can also be inserted into additional vertebrae 50 as needed to alleviate scoliosis.

Figure 2:
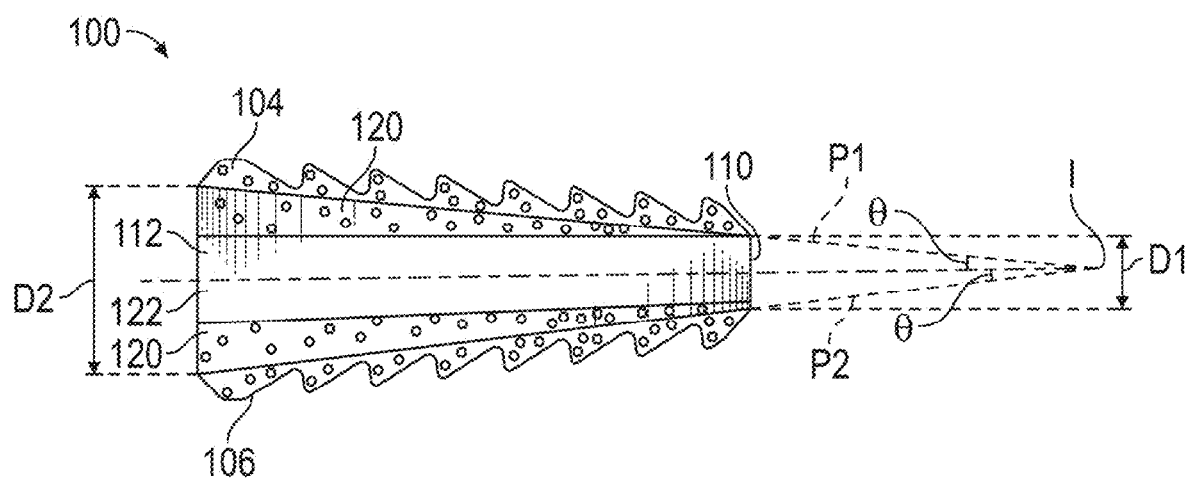
FIG. 2 shows a lateral side elevational view of the wedge implant shown in FIG. 1.
Figure 3:
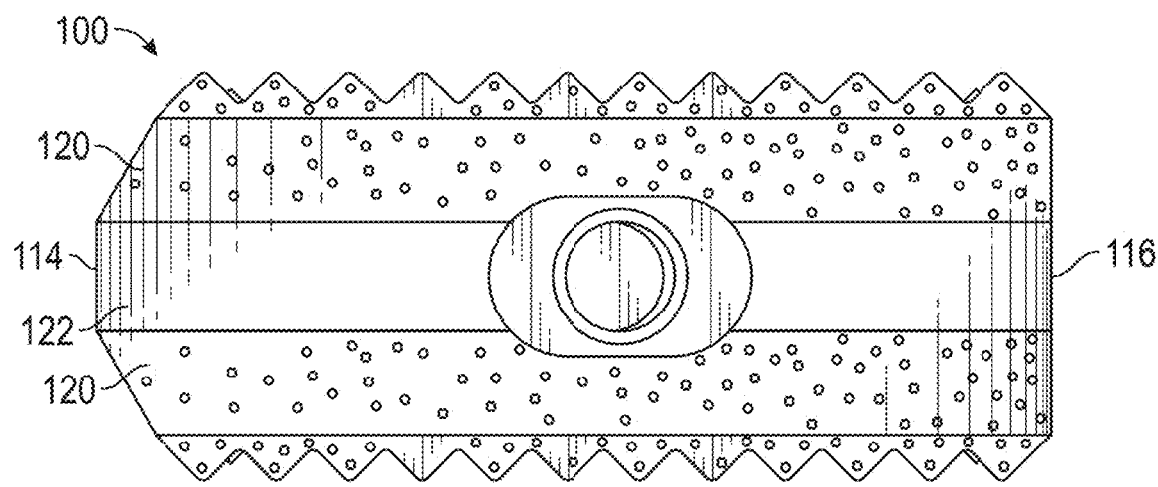
FIG. 3 shows a posterior side elevational view of the wedge implant shown in FIG. 1.

Wedge implant 100 includes an outer perimeter 102 that defines implant 100. Wedge implant 100 also includes a top surface 104 extending generally in a first plane P1 and a bottom surface 106 extending in a second plane P2. Second plane P2 extends obliquely with respect to first plane P1. As shown in FIG. 2, first plane P1 intersects second plane P2 at a location "I" outside outer perimeter 102 of implant 100. Top surface 104 and bottom surface 106 can be planar surfaces. Alternatively, top surface 104 and bottom surface 106 can have other shapes, such as, for example, domed surfaces.

A medial surface 110 extends between top surface 104 and bottom surface 106 proximate to the intersection of first plane P1 and second plane P2. A lateral surface 112 extends between top surface 104 and bottom surface 106 distal from the intersection of first plane P1 and second plane P2. An anterior surface 114 extends a first distance D1 between top surface 102 and bottom surface 104 between medial surface 110 and lateral surface 112. Anterior surface 114 extends generally a constant first distance D1 across its length. A posterior surface 116 extends a second distance D2 between top surface 104 and bottom surface 106 between medial surface 110 and lateral surface 112. Posterior surface 116 extends generally a constant second distance D2 across its length. Second distance D2 is greater than first distance D1.

Figure 7:
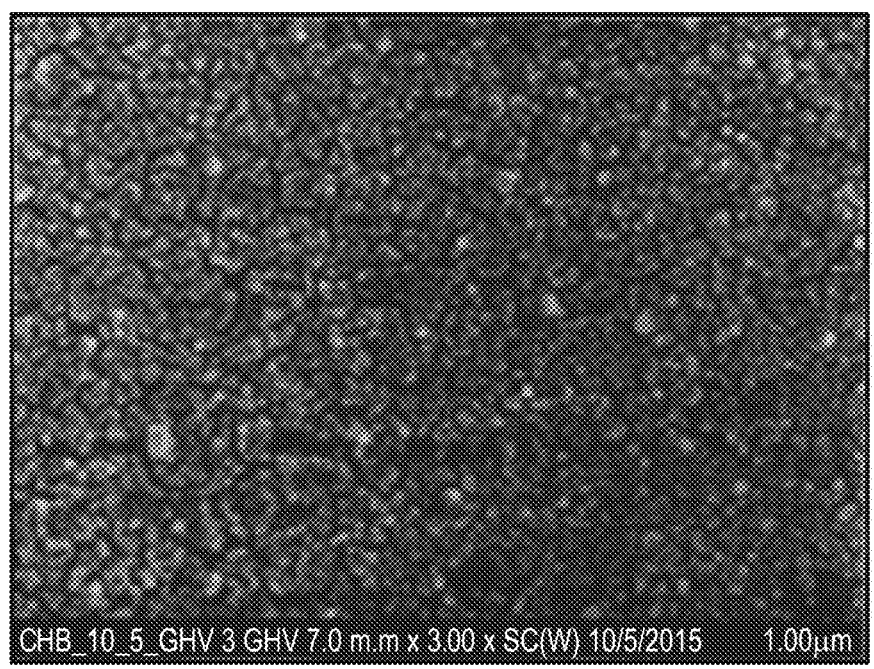
FIG. 7 shows an enlarged view of an osteointegration surface used to coat a portion of the wedge implant shown in FIG. 1.

In an exemplary embodiment, body 102 is constructed from a material having a relatively low stiffness, such as, for example, poly-ether-ether ketone ("PEEK"), which has a modulus of elasticity about 3.6 GPa. In an exemplary embodiment, an antimicrobial and/or osteointegration surface 120, shown in detail in FIG. 7, can be disposed on each of top surface 104 and bottom surface 106. In an exemplary embodiment, the osteointegration portion of surface 120 can be titanium and the antimicrobial portion of surface 120 can be silver or titanium nanotextured or titanium oxide nanostructured.

Osteointegration surface 120 extends downwardly from top surface 104 along medial surface 110, lateral surface 112, anterior surface 114, and posterior surface 116 only a portion of the way to bottom surface 106. Similarly, osteointegration surface 120 can extend upwardly from bottom surface 106 along medial surface 110, lateral surface 112, anterior surface 114, and posterior surface 116 only a portion of the way to top surface 104, resulting in a band 122 around outer perimeter 102 of implant 100 that is free from osteointegration surface 120. In an exemplary embodiment, band 122 has a cranial-to-caudal dimension of about 0.01 mm. Alternatively, band 122 can have a cranial-to-caudal dimension of greater than about 0.1 mm. The existence of band 122 allows for flexing of implant 100, which is softer with a lower modulus of elasticity than osteointegration surface 120, without loading compressive forces onto osteointegration surface 120.

Figure 5:
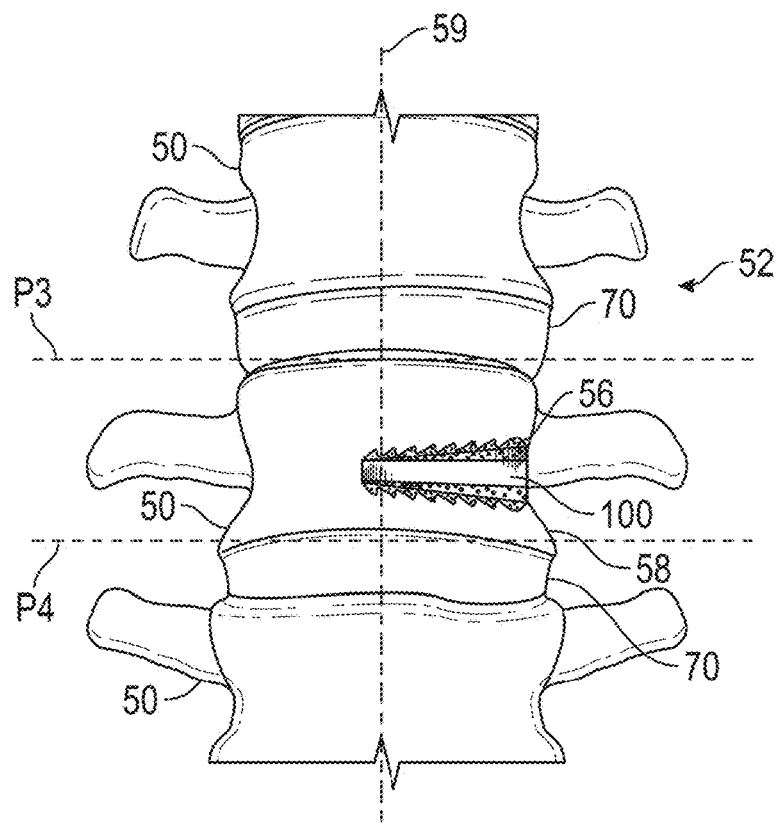
FIG. 5 shows a posterior side elevational view of the wedge implant shown in FIG. 1 inserted into a vertebra a spinal column.

To correct adult or pediatric scoliosis deformity, implant 100 can be inserted into vertebra 50 in a lateral-to-medial direction to realign spine 52 with the craniocaudal axis 59, as shown in FIG. 5. To insert wedge 100, an osteotomy is performed on vertebra 50 by making an incision 56 in vertebra 50. In an exemplary embodiment, the insertion 56 can be made from lateral side 58 of vertebra 50 inwardly toward the center of vertebra 50, and inserting implant 100 into incision 56. Alternatively, incision 56 may be made to the contralateral side of vertebra 50, with implant 100 being inserted therein. In pediatric patients, the osteotomy is formed in a way not violate the growth plate of vertebra 50. This insertion effectively pivots cranial plane P3 relative to caudal plane P4 of vertebra 50 in an effort to make cranial plane P3 and caudal plane P4 closer to match the crainocaudal axis of spine 52 and aligned in the sagittal plane.

Figure 4:
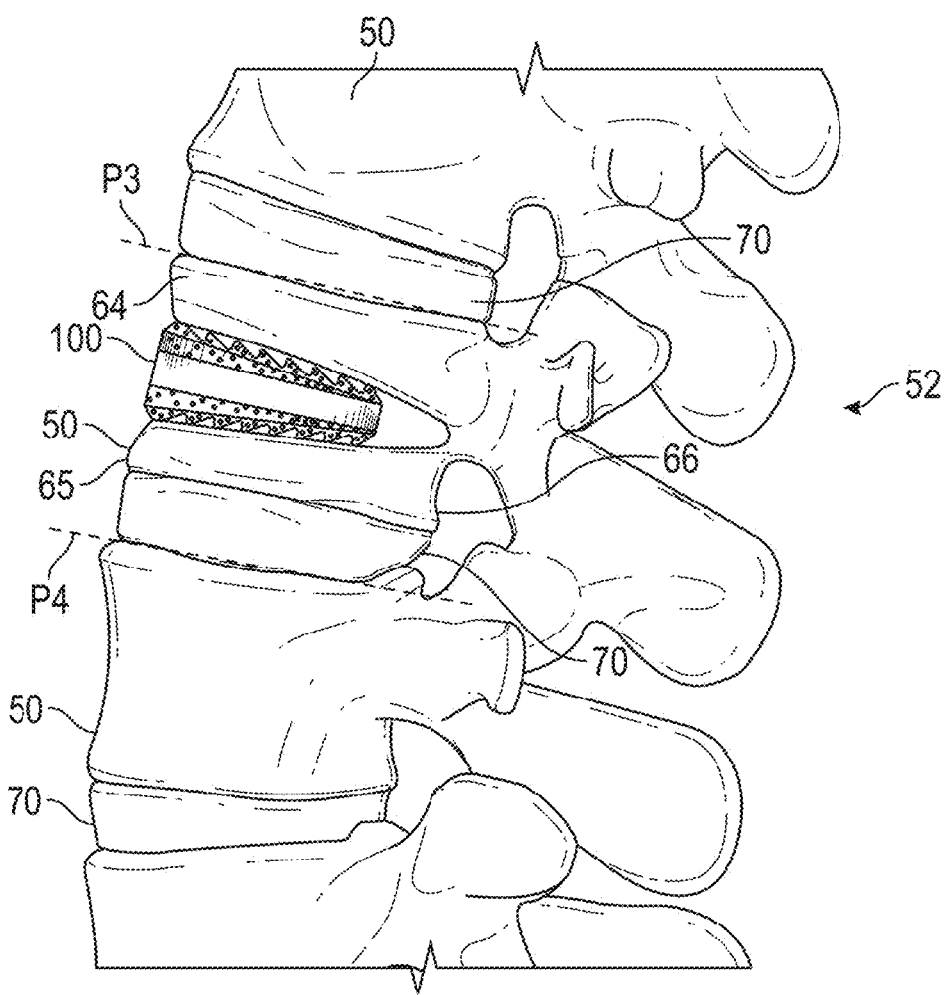
FIG. 4 shows a lateral side elevational view of the wedge implant shown in FIG. 1 inserted into a vertebra in a spinal column.

Similarly, to correct adult or pediatric scoliosis deformity, implant 100 can be inserted into vertebra 50 in a anterior-to-posterior direction to restore lordosis or kyphosis of the spine, as shown in FIG. 4. To insert wedge 100, an osteotomy is performed on vertebra 50 by making an incision 64 in vertebra 50 from posterior side 65 of vertebra 50 inwardly toward anterior side 66 of vertebra 50, and inserting implant 100 into incision 64. This insertion effectively pivots cranial plane P3 relative to caudal plane P4 in an effort to make cranial plane P3 and caudal plane P4 closer to normal conditions to restore lordotic or kyphotic angulation the spine 52.

Figure 6:
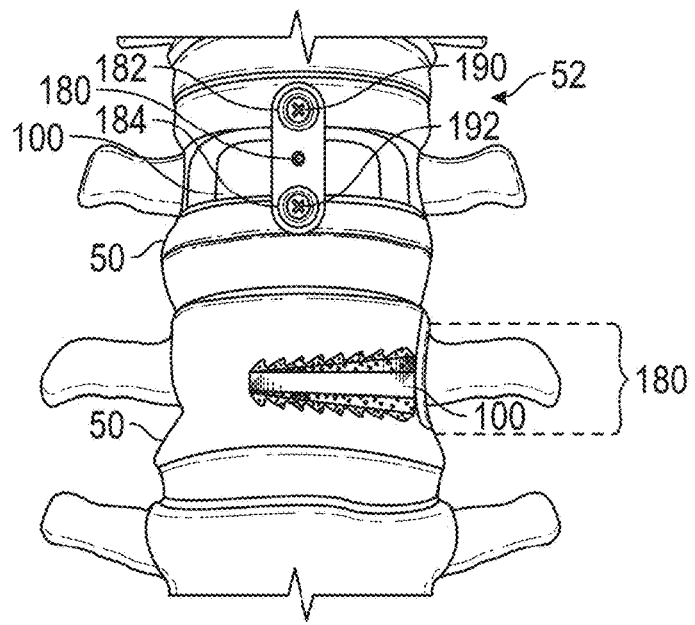
FIG. 6 shows a retaining plate used to retain the wedge implant shown in FIG. 1 in the vertebrae shown in FIGS. 4 and 5.

In either of the above two procedures, a retaining plate 180 is fixed to vertebra 50 to secure implant 100 to vertebra 50. FIG. 6 shows retaining plate 180 being used to secure implant 100 inserted in the posterior-to-anterior direction in top vertebra 50, and retaining plate 180 used to secure implant 100 inserted in the lateral-to-medial direction. The retaining plate 180 is shown in both anterior-posterior and medial-lateral alignment. However a surgeon will generally only insert retaining plate 180 from one direction in vertebra 50 or adjacent vertebrae 50.

Retaining plate 180 is an elongate member with a first hole 182 at a first end 184 thereof and a second hole 186 at a second end 188 thereof. A first screw 190 is inserted through first hole 182 and into vertebra 50 toward or parallel with cranial plane P3, while a second screw 192 is inserted through second hole 186 and into vertebra 50 toward parallel with caudal plane P4. In an exemplary embodiment, retaining plate 180 and screws 190, 192 can be made from standard biomaterials, such as titanium, or bio-resorbable materials, such as, for example, magnesium-based alloys that will ultimately dissolve by the time implant 100 has been fully engaged by vertebra 50.

Figure 6A:
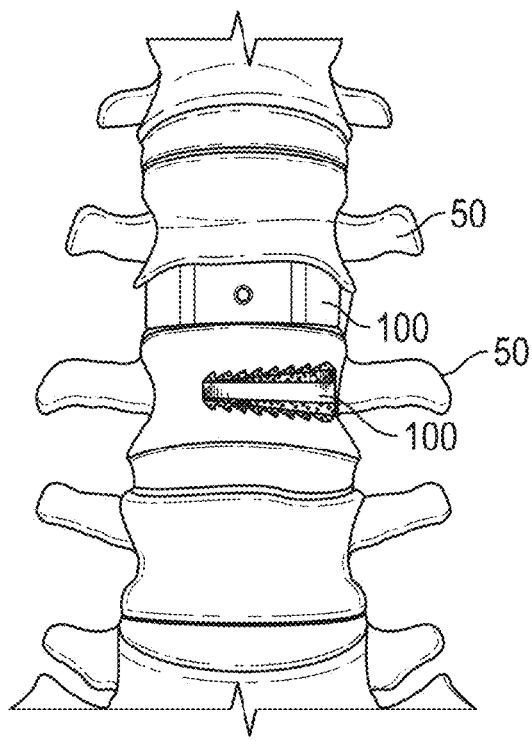
FIG. 6A shows a lateral side elevational view of the wedge implant shown in FIG. 1 inserted between adjacent vertebrae in a spinal column.

While an exemplary use of implant 100 as described above is used in a single vertebra 50, those skilled in the art will recognize that in some cases, it may be more advantageous to remove a disk 70 between two adjacent vertebrae 50 and insert implant 100 between the two adjacent vertebrae 50, as an interbody implant, as shown in FIG. 6A. In such a case, screw 190 for plate 180 can be secured into the upper vertebra 50 and screw 192 for plate 180 can be secured into the lower vertebra 50.

In an exemplary embodiment, it may be necessary to remove at least a lower portion of the upper vertebra 50 and an upper portion of the lower vertebra 50 in order to properly insert implant 100.

Figure 8:
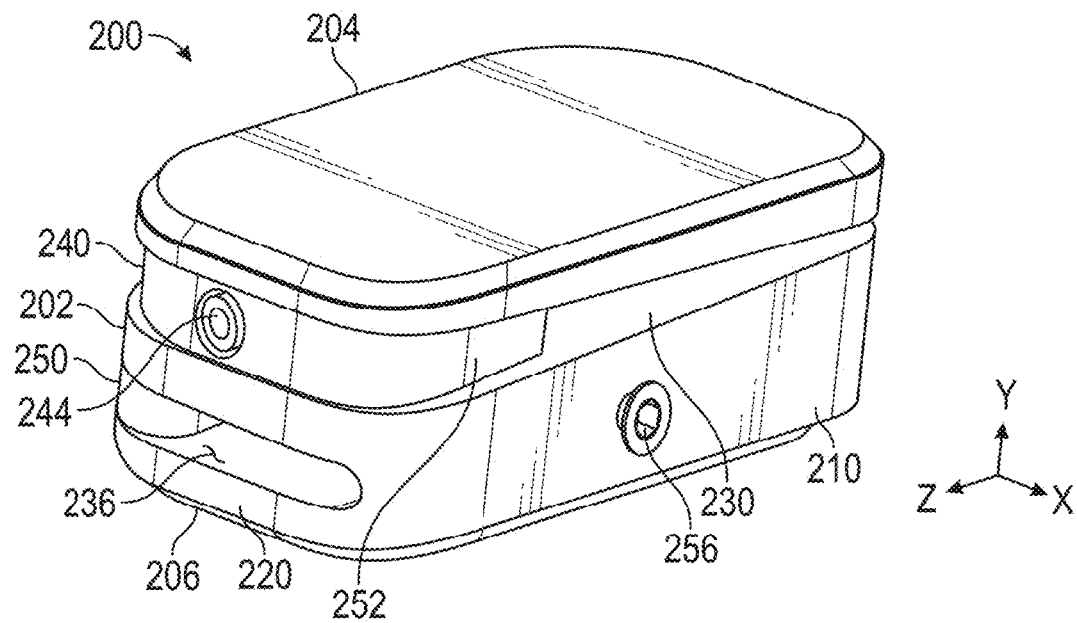
FIG. 8 shows a perspective view of a wedge implant assembly according to a second exemplary embodiment of the present invention.
Figure 9:
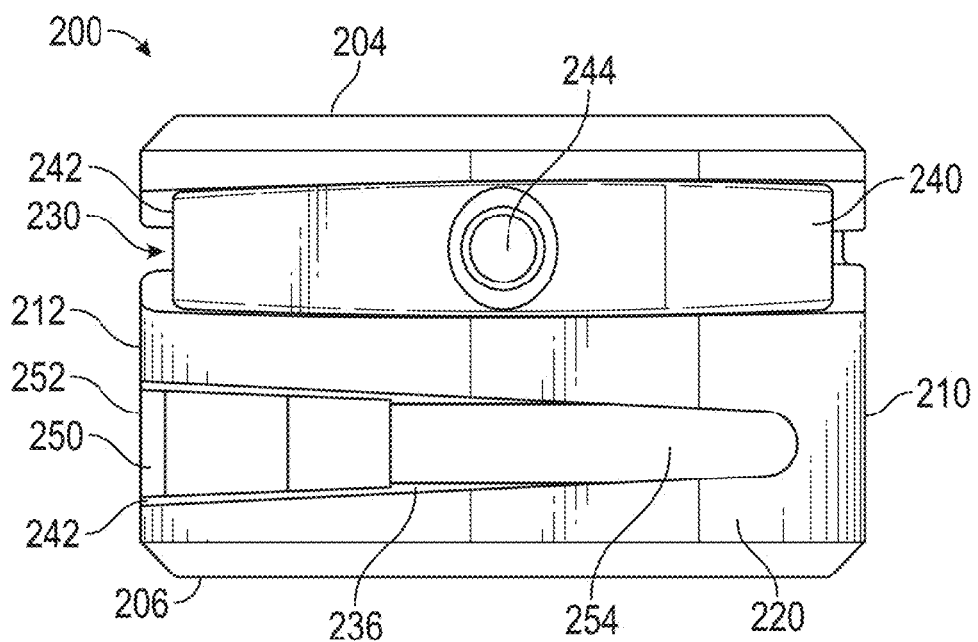
FIG. 9 shows a lateral elevational view of the wedge implant assembly shown in FIG. 8.
Figure 10:
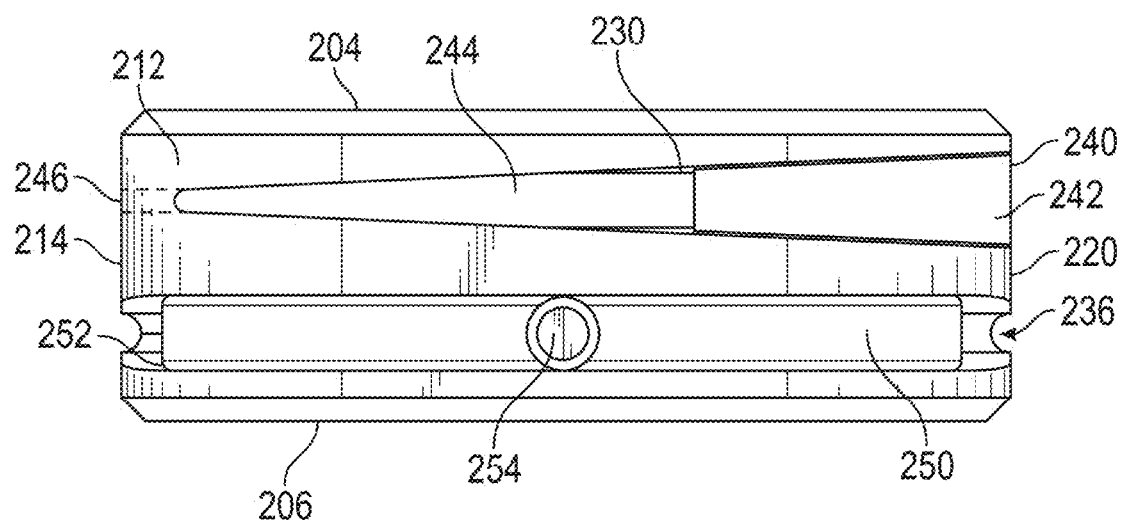
FIG. 10 shows a posterior elevational view of the wedge implant assembly shown in FIG. 8.

In an alternative embodiment, referring to FIGS. 8-10, a bi-planar adjustable implant 200 according to an exemplary embodiment of the present invention is shown. Implant 200 can be inserted into an osteotomy in vertebra 50 as discussed above with respect to implant 100. Alternatively, as also discussed above with respect to implant 100, upon removal of a disk between two adjacent vertebrae 50, implant 200 can be inserted into the space between the two vertebrae 50.

Implant 200 includes a body 202 having a top surface 204 and a bottom surface 206, distal from top surface 204. Top surface 204 and bottom surface 206 can be planar surfaces. Alternatively, top surface 204 and bottom surface 206 can have other shapes, such as, for example, domed surfaces.

A medial side 214 connects top surface 204 and bottom surface 206. A lateral side 220 is located distal from medial side 214. An anterior side 210 extends between medial side 214 and lateral side 220 such that anterior side 210 connects top surface 204 and bottom surface 206 to each other. A posterior side 212 extends between lateral side 220 and medial side 214, distal from anterior side 210.

Implant 200 has a first slot 230 extending from lateral side 220 toward medial side 214 and a second slot 236 extending from posterior side 220 toward anterior side 214. Slots 230, 236 allow for the insertion of wedges to alter the angle of the plane of top surface 204 with respect to bottom surface 206. The location of slot 230 relative to slot 236 allows for the adjustment of top surface 204 relative to bottom surface 206 about two axes, namely, the x and z axes as shown in FIG. 8.

A first wedge assembly 240 is inserted into first slot 230. As used herein, the term "wedge assembly" means any device, inserted in an implant, that can be manipulated to change the angle of at least one face of the implant. First wedge assembly 240 has a first member 242 translatable in a lateral-to-medial direction. In an exemplary embodiment, first member 242 is a wedge having a tapered profile from the lateral direction to the medial direction as shown in FIG. 9. A second member 244 is operatively connected to first member 242 such that operation of second member 244 translates first member 240 in the lateral-to-medial direction. In an exemplary embodiment, second member 244 can be a screw threadedly inserted through first member 242, such that rotation of second member 244 about the "Z" axis translates first member 242 in the "Z" direction. Second member 244 can include an adjusting mechanism 246, such as, for example, a screw head, extending from anterior side 214.

Similarly, a second wedge assembly 250 is inserted into second slot 236. Second wedge assembly 250 has a first member 252 translatable in a posterior-to-anterior direction. Similar to first wedge assembly 240, first member 252 is a wedge having a tapered profile from the lateral direction to the medial direction as shown in FIG. 10. A second member 254 is operatively connected to first member 252 such that operation of second member 254 translates first member 250 in the posterior-to-anterior direction. In an exemplary embodiment, second member 254 can also be a screw threadedly inserted through first member 252, such that rotation of second member 254 about the "X" axis translates second member 252 in the "X" direction. Second member 254 can include an adjusting mechanism 256, such as, for example, a screw head, extending from anterior side 210.

Translation of first member 242 of first wedge assembly 240 pivots top surface 204 with respect to bottom surface 206 about medial side 214 and translation of first member 252 of second wedge assembly 250 pivots top surface 204 with respect to bottom surface 206 about anterior side 210.

Figure 11:
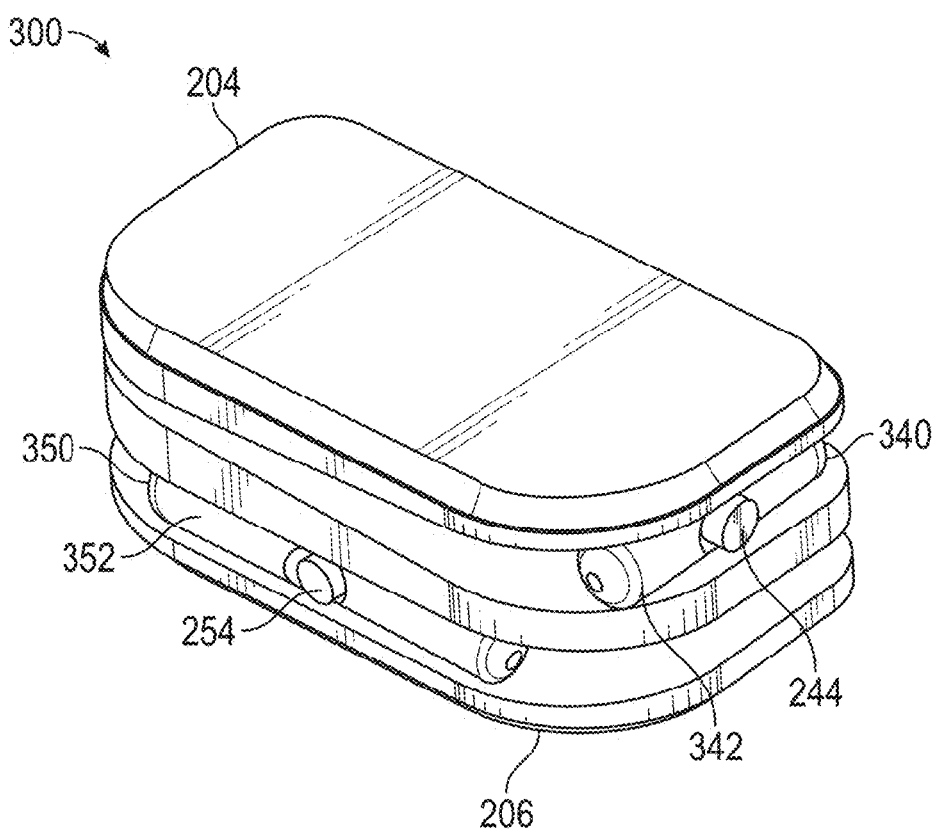
FIG. 11 shows a perspective view of a wedge implant assembly according to a third exemplary embodiment of the present invention.
Figure 12:
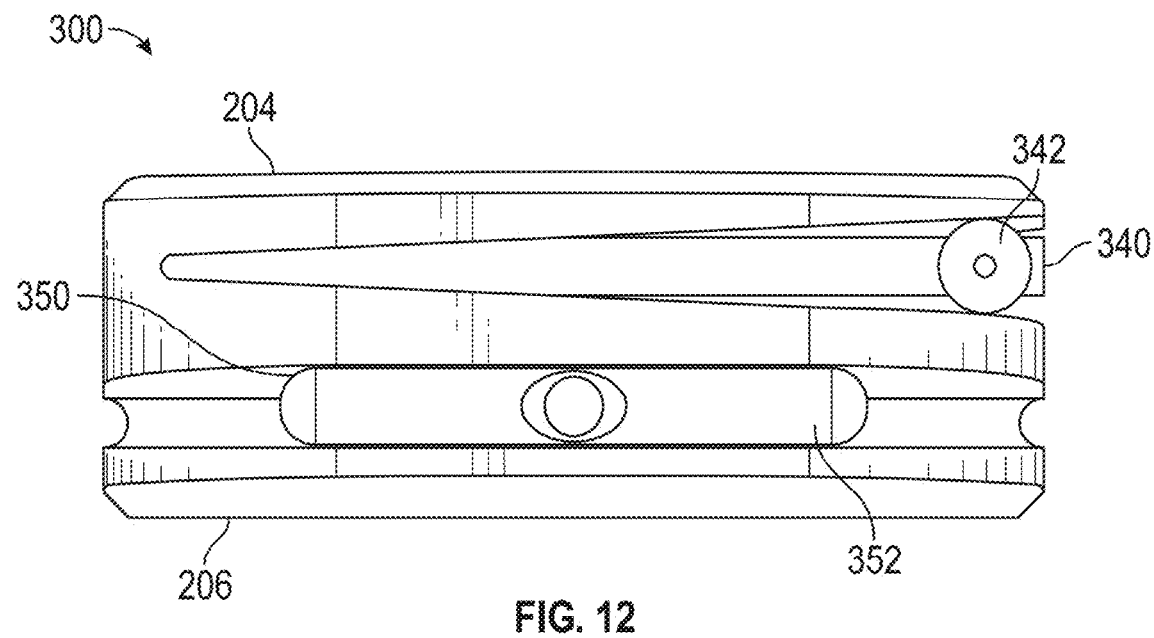
FIG. 12 shows a posterior elevational view of the wedge implant assembly shown in FIG. 11.
Figure 13:
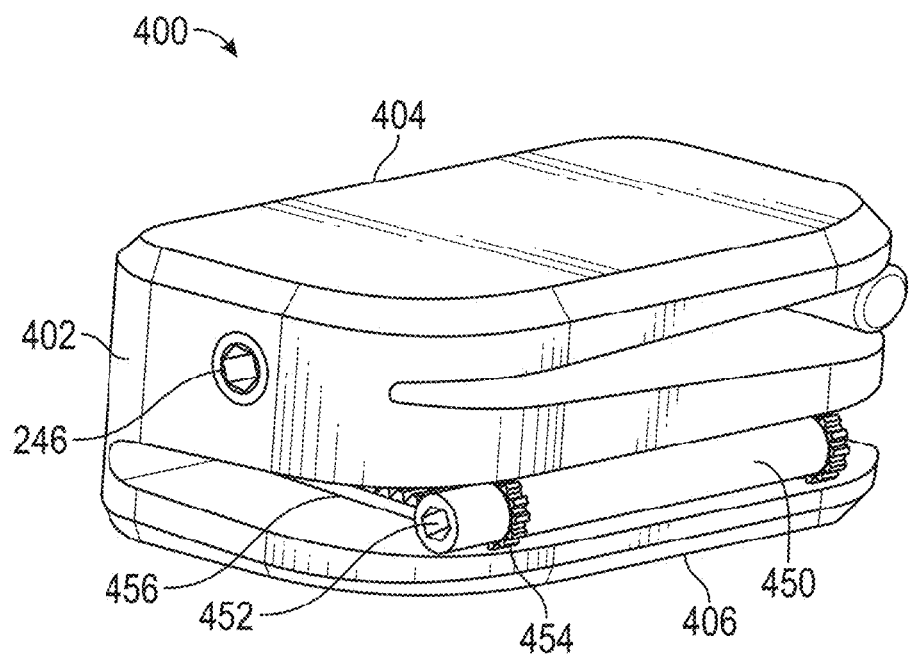
FIG. 13 shows a perspective view of a wedge implant assembly according to a fourth exemplary embodiment of the present invention.
Figure 14:
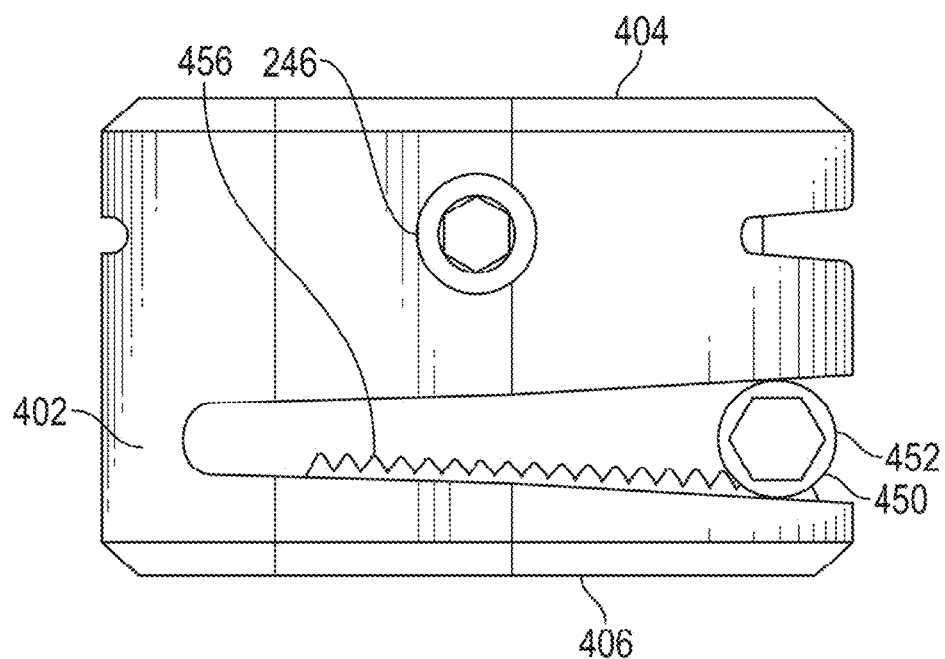
FIG. 14 shows a medial side elevational view of the wedge implant assembly shown in FIG. 13.
Figure 15:
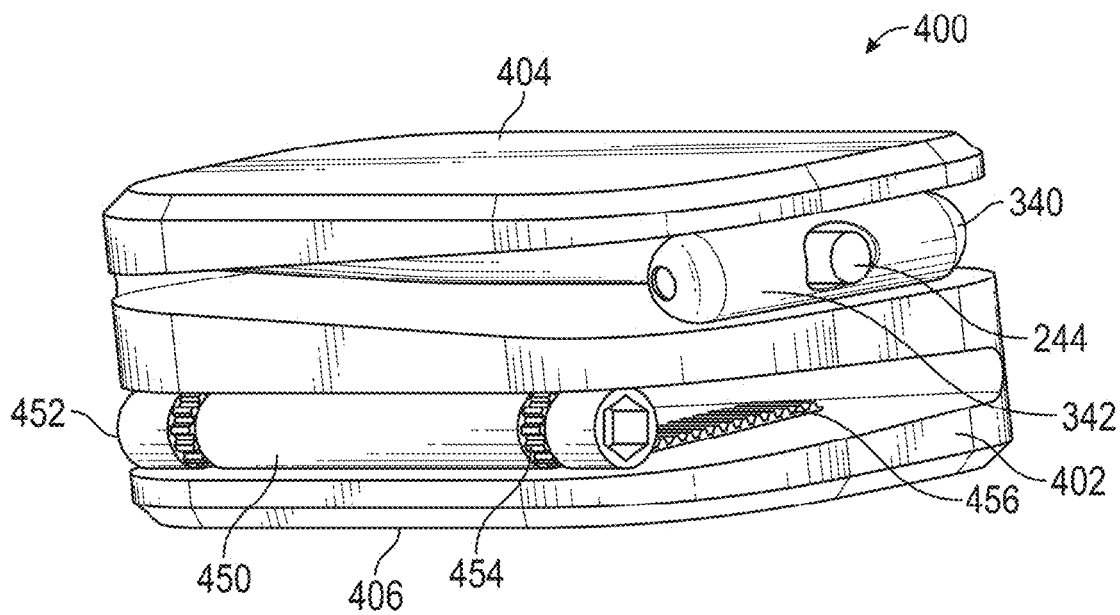
FIG. 15 shows a rear perspective view of the wedge implant assembly shown in FIG. 13.
Figure 16:
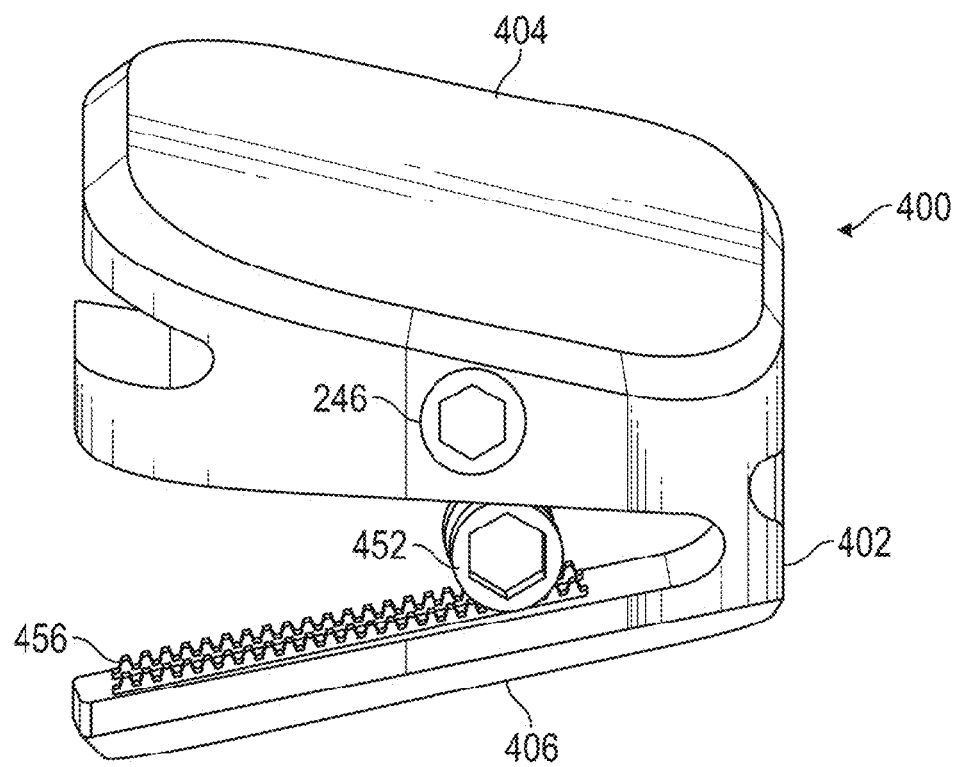
FIG. 16 shows a lateral side elevational view of the wedge implant assembly shown in FIG. 15.
Figure 17:
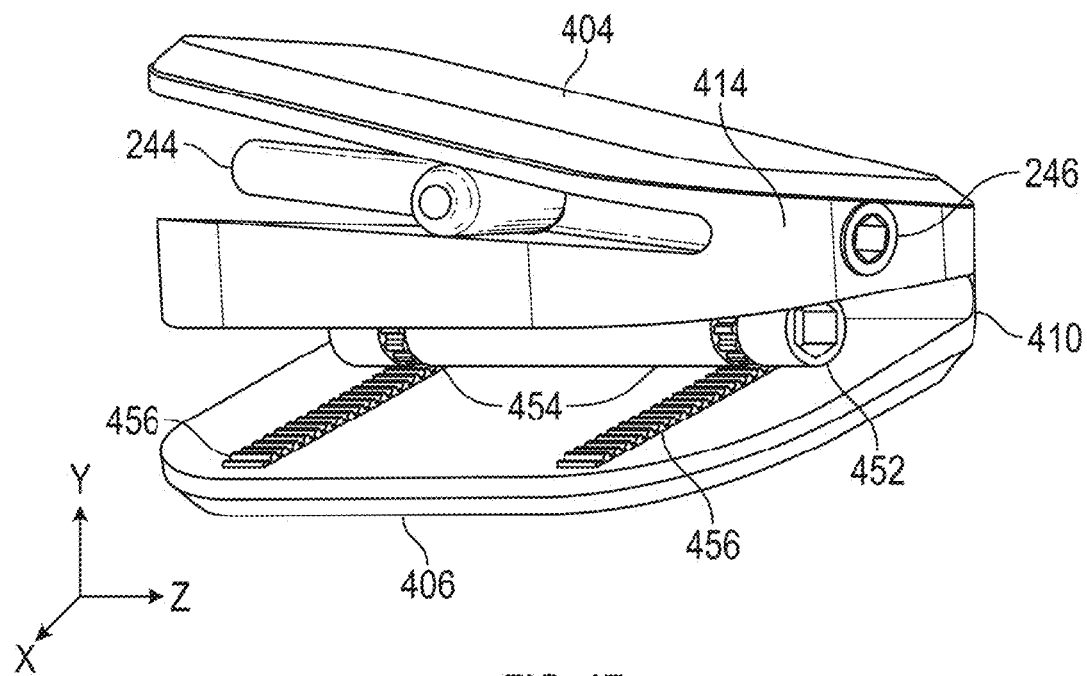
FIG. 17 shows a rear perspective view of the wedge implant assembly shown in FIG. 15, with a second wedge assembly actuated to adjust the tilt angle of the top surface of the wedge implant assembly.

In an alternative exemplary embodiment of a wedge assembly 300, shown in FIGS. 11 and 12, instead of the wedge provided as first member 242 and 252, wedge assemblies 340, 350 utilize a cylinder 342, 352. Second member 244, 254 from wedge assembly 200 can be used to activate cylinder 342, 352, respectively. It is noted, however, that for either wedge assembly 200 or wedge assembly 300, first wedge assembly 240 is actuated from lateral side 220 while second wedge assembly 250 is actuated from posterior side 212. It is desired to be able to actuate both first wedge assembly 240 and second wedge assembly 250 from the same side in order to minimize incisions made into the patient. Therefore, if wedge assembly 200, 300 is inserted from the lateral side of vertebra 50, it is desired to be able to actuate first wedge assembly 240 and second wedge assembly 250 from the lateral side of vertebra 50. Therefore, to actuate second wedge assembly, it may be desired to use a driver (not shown) having a right angle drive.

An alternative embodiment of an implant assembly 400 according to the present invention is shown in FIGS. 13-17. Implant assembly 400 is similar to implant assembly 300, with the exception of, instead of second wedge assembly 350, a second wedge assembly 450 is provided. Second wedge assembly 450 includes a first member 452, which is a cylinder having a plurality of gear teeth 454 formed around an exterior perimeter thereof. Second wedge assembly 450 includes a second member fixedly 456 connected to body 402 of implant assembly 400. In an exemplary embodiment, second member 456 is a toothed rack engageable with gear teeth 454 of first member 452 such that, when first member 452 is rotated, gear teeth 454 translates first member 452 along second member 456. An exemplary embodiment, as shown FIG. 17, two sets of gear teeth 454 are formed on first member 452 and two sets of toothed racks of second member 456 are connected to body 402, although those skilled in the art will recognize that more or less than two sets can be used.

An advantage of implant assembly 400 is that first member 342. A first wedge assembly 340, and first member 452 of second wedge assembly 450 can both be actuated from the same side of the patient, such as, for example, the lateral side.

Translation of first member 342 of first wedge assembly 340 pivots top surface 404 with respect to bottom surface 406 about medial side 414 and translation of first member 252 of second wedge assembly 250 pivots top surface 204 with respect to bottom surface 206 about anterior side 410.

Also, similar to wedge implant 100, wedge implant assembly 200, 300, 400 can include an antimicrobial and/or osteointegration surface disposed on top and bottom surfaces thereof, with only a portion of each of the medial side, the lateral side, the anterior side, and the posterior side, including the osteointegration surface disposed thereon.

Figure 18:
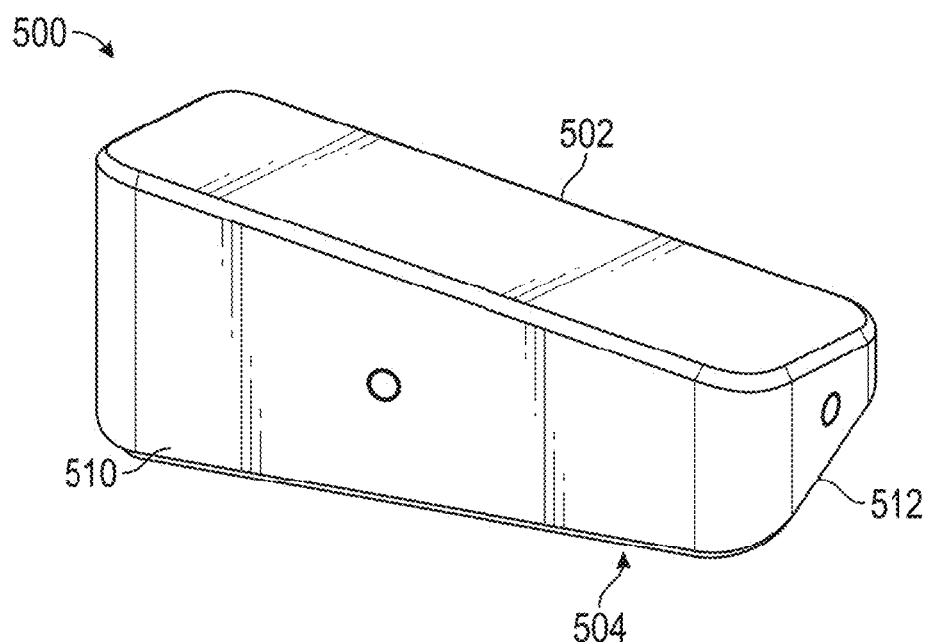
FIG. 18 shows a perspective view of a wedge implant assembly according to a fifth exemplary embodiment of the present invention.
Figure 19:
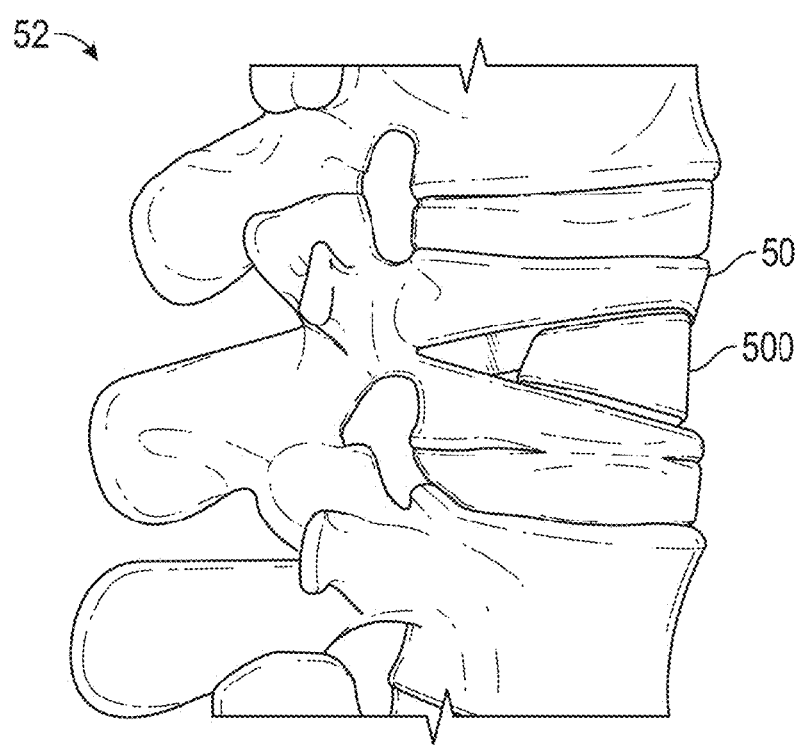
FIG. 19 shows a right side elevational view of the wedge implant assembly shown in FIG. 18 inserted into a vertebra of a patient.
Figure 20:
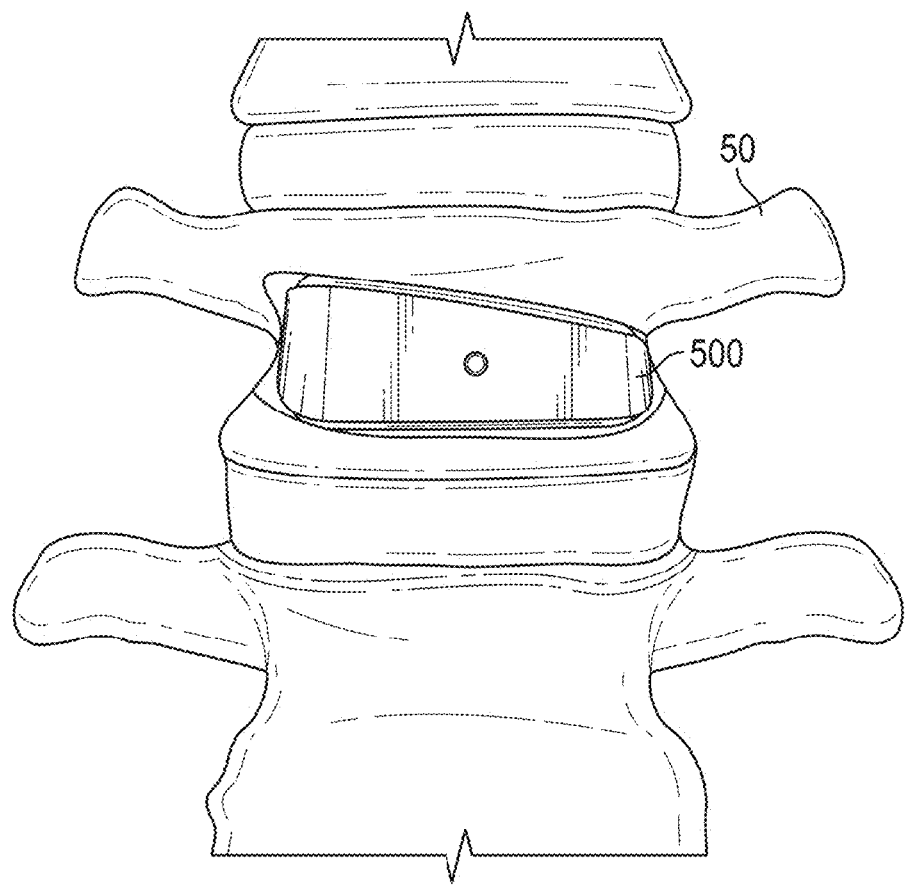
FIG. 20 shows a posterior side elevational view of the wedge implant assembly and vertebra shown in FIG. 19.
Figure 21:
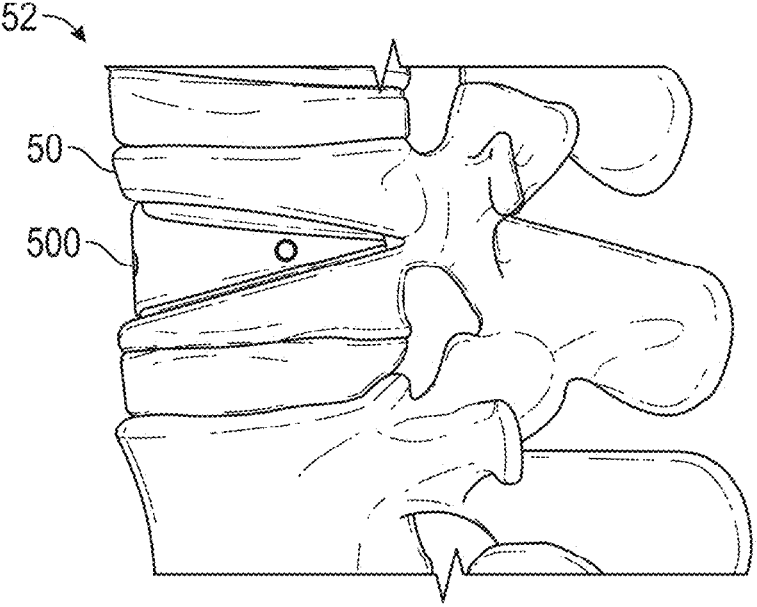
FIG. 21 shows a left side elevational view of the wedge implant assembly, and vertebra shown in FIG. 19.

An alternative embodiment of an implant assembly 500 according to the present invention is shown in FIGS. 18-22. Implant assembly 500 is a non-adjustable bi-planar wedge. Wedge 500 is similar to wedge 100, but, instead of anterior surface 114 extending generally a constant first distance D1 across its length and posterior surface 116 extending generally a constant second distance D2 across its length, as shown in FIG. 18, at least two adjacent surfaces taper from larger to smaller, forming a bi-planar top surface 502.

By way of example only, posterior surface 510 tapers from larger to smaller in a left-to-right direction and lateral surface 512 tapers from larger to smaller in a posterior-to-anterior direction, resulting in wedge assembly 500 that can be implanted into vertebra 50, as shown in FIGS. 19-22. An advantage of wedge assembly 500 is that wedge assembly 500 can be used to simultaneously correct a spinal column 52 that has abnormal curvature into the lateral-to-medial direction as well as in the posterior-to-anterior direction. Optionally, although not shown, a retaining plate 180 can be used to secure wedge assembly 500 in vertebra 50.

Figure 22:
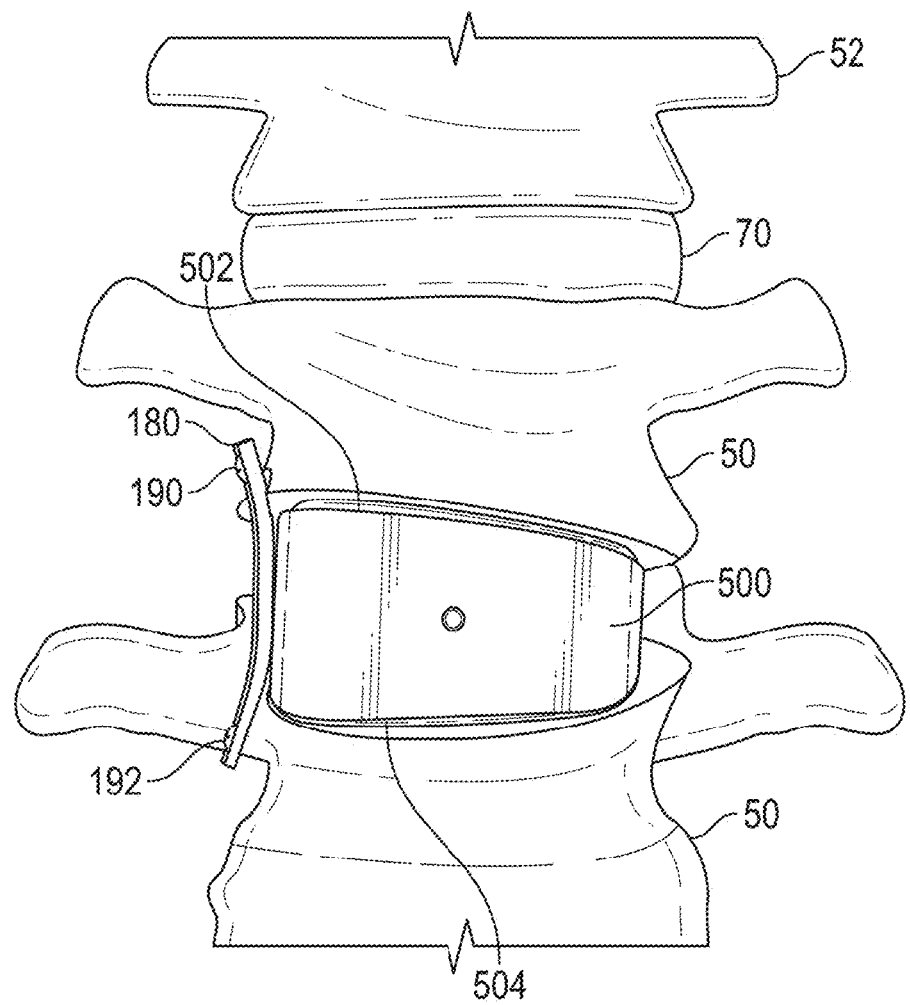
FIG. 22 shows a posterior side elevational view of the wedge implant assembly shown in FIG. 18, inserted between two adjacent vertebrae.

FIG. 22 shows wedge assembly 500 inserted between two adjacent vertebrae 50 with a disk, similar to disc 70 previously disposed between the adjacent vertebrae 50, having been removed and wedge assembly 500 inserted therein. Optionally, plate 180 can be used to secure wedge assembly 500 between the adjacent vertebrae 50 using screw 190 to secured plate 180 to the upper vertebra 50 and screw 192 to secure plate 180 to the lower vertebra 50. As shown FIG. 22, plate 180 is attached to a lateral side of spine 52. Those skilled in the art, however, will recognize that plate 180 can also be attached to spine 152 along the posterior side of spine 52.

As used herein, the term "medical device" means a medical implant, an insertion or other type of tool, or any other item that contacts or is inserted into a patient, including, but not limited to, the devices and structures described above.

The medical device can be treated with a surface treatment that performs and/or achieves one or more of the following purposes: inhibition of microbial, bacterial, and other types of unwanted adhesion on the surface; inhibition of microbial, bacterial, and other types of unwanted growth on the surface; and enhanced osteointegration with bone and other types of living matter. Osteointegration can be defined as a "direct structural and functional connection between ordered living material, such as bone, and the surface of a load-carrying or other type of implant."

FIGS. 23A-D are confocal images showing *S. aureus* colony forming units on (a) untreated Ti and (b) treated $TiO_2$ after 16 hours of incubation. SEM images show the (c) untreated Ti surface and the (d) treated $TiO_2$ surface. While $TiO_2$ was used to show the effectiveness of a treated surface with respect to bacteria, such as *S. aureus*, those skilled in the art will recognize that other bacteria, microbes, and other unwanted growths can be inhibited and even killed using other nanofeatures such as non-$TiO_2$ or non-oxides on an exposed surface. Examples of non-titanium base oxides can be $AgO_2$, while examples of non-oxides can by hydroxyapatite (HA) or $CaPO_4$. As used herein, the term "nanofeatures" is used to mean nanoparticles, nanotexturing, or other application to or modification of a surface that results in nano-sized fetaures or irregularties being present on the surface.

Figure 24:
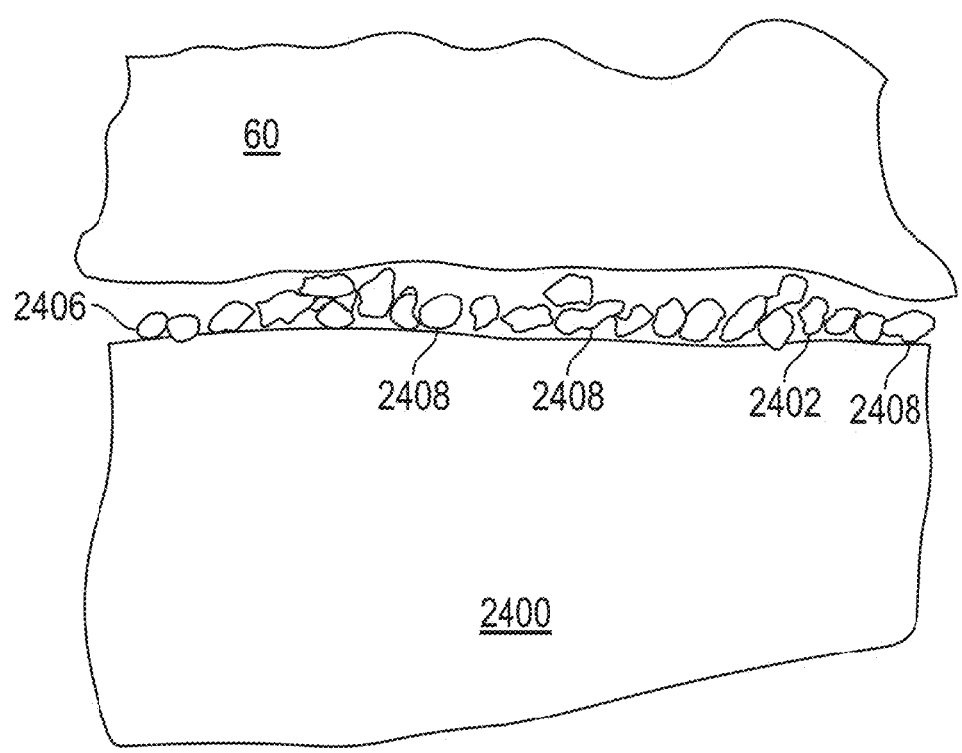
FIG. 24 shows a side elevational view of a treated substrate according to an exemplary embodiment of the present invention.

Referring to FIG. 24, a medical device 2400 includes a substrate 2402 having an exposed surface 2404. Substrate 2402 can be constructed from a metallic material such as, for example, titanium or some other biocompatible material. Alternatively, substrate 2402 can be constructed from a non-metallic material such as, for example, polyether ether ketone (PEEK) or some other biocompatible material. Still alternatively, substrate 2402 can be constructed from a mix/combination of metallic and non-metallic materials.

A texture 2406 is formed over at least part of exposed surface 2404. Texture 2406 comprises a plurality of nanofeatures 2408 that can inhibit bacterial adhesion and/or growth on surface 2404. Additionally, nanofeatures 2408 can promote osteointegration with adjoining tissue 60.

In an exemplary embodiment, nanofeatures 2408 have a size range between about 0.1 nanometers and about 1,000 nanometers. In another exemplary embodiment, nanofeatures 2408 have a size range between about 20 nanometers and about 50 nanometers and in yet another exemplary embodiment, nanofeatures 2408 have a size range between about 0.1 nanometers and about 10 nanometers.

In an exemplary embodiment, texture 2406 comprises an oxide, such as, for example, a titanium oxide or a titanium dioxide, although those skilled in the art will recognize that other types of oxides or even non-oxides can be provided as texture 2406.

In a further exemplary embodiment, texture 2406 comprises the deposition of a coating of an oxide (or other nanofeatured material) onto substrate 2402. In an exemplary embodiment of a deposition method, nanophase titanium dioxide was synthesized using a wet chemical synthesis and was deposited on Ti-6Al-4V titanium screws (equivalent to substrate 2402) using a cathodic arc deposition plasma system. Bacterial assays were conducted using *Staphylococcus aureus* (ATCC® 29740™), *Pseudomonas aeruginosa* (ATCC® 39324™) and an ampicillin resistant strain of *E. coli* (BIO-RAD Strain HB101 K-12 #166-0408 and pGLO Plasmid #166-0405). 0.03% tryptic soy broth (TSB) (Sigma Aldrich, Cat #22092) and agar (Sigma-Aldrich, Cat # A1296) were used as the media and colony forming assays were performed to determine bacterial adhesion.

Nanophase titanium dioxide was successfully synthesized and applied onto the desired exposed surface of a substrate. A statistically significant decrease in bacterial adhesion was observed across all 3 strains of bacteria; an example of confocal images for S. *Aureus* is given in FIGS. 23A-D. In addition, decreased macrophage functions and increase osteoblast functions were also observed in the nano TiO2 treated Ti6Al4V screws. It is noted that this was all achieved without the use of drugs and/or antibiotics, decreasing the chance for the spread of antibiotic resistant bacteria and drug side effects.

An alternative method or nanotexturing surface 2404 is by surface etching or otherwise treating surface 2404 according to known methods. For example, a titanium surface can be bombarded with oxygen to simultaneously texturize and oxidize surface 2404 such that the nanofeatures are formed from substrate 2402 itself.

Figure 25:
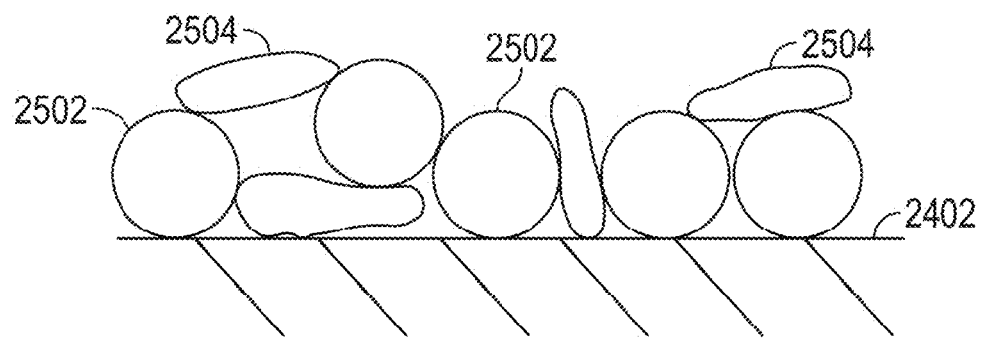
FIG. 25 shows a side elevational view of a treated substrate according to another exemplary embodiment of the present invention.

Referring to FIG. 25, nanoparticles having a first particle size range 2502 and a second particle size range 2504 can by mixed together and randomly applied to substrate 2402. Alternatively, referring to FIG. 26, nanoparticles having a first size range 2502 (such as, for example, about 100 nanometers) can be applied to substrate 2402 and then nanoparticles having a second size range 2504 (such as, for example, about 5 nanometers) can be applied on top of the nanoparticles having the first size range 2502.

Figure 26:
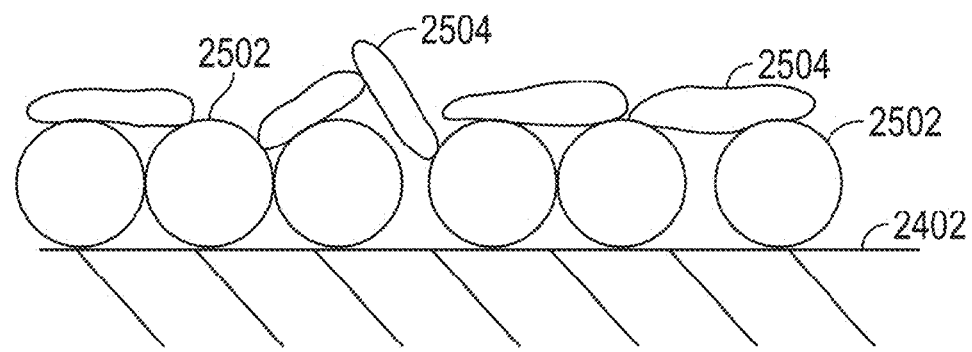
FIG. 26 shows a side elevational view of a treated substrate according to still another exemplary embodiment of the present invention.

As shown in FIGS. 25 and 26, nanoparticles 2502, 2504 can be different shapes. Although spherical nanoparticles 2502 and elongated nanoparticles 2504 are shown, those skilled in the art will recognize that the nanoparticles can be other shapes, such as, for example, irregularly shaped, nanotubular, or other shapes.

Figure 27:
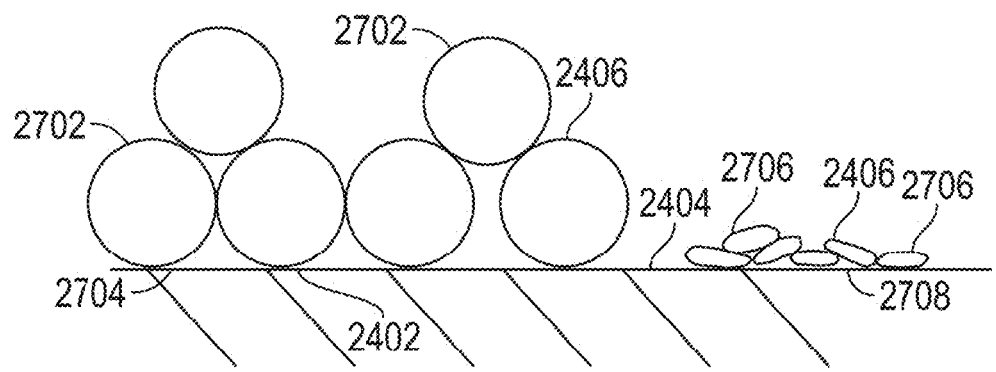
FIG. 27 shows a side elevational view of a treated substrate according to another exemplary embodiment of the present invention.

FIG. 27 shows nanoparticles of differing size ranges being applied to different locations on substrate 2402. Nanofeatures 2702 at a first location 2704 have a first size range and nanofeatures 2706 at a second location 2708 have a second size range, different from the first size range. Optionally, as shown in FIG. 27, nanofeatures 2702 at first location 2704 have a first shape, and nanofeatures 2706 at second location 2708 have a second shape, different from the first shape.

The features shown in FIG. 27 can be formed by masking second location 2708 of substrate 2402 with a mask so that nanofeatures cannot be applied to second location 2708. Nanofeatures 2702 are then applied to the exposed (first location 2704) portion of substrate 2402.

Then, the mask is removed from second location 2708 and a second mask is applied over first location 2704 and nanofeatures 2706 are then applied to the exposed (second location 2708) portion of substrate 2402.

The material used for the mask can be bees wax, fish glue, coconut oil, sequential dipping, tape, plastic caps, metallic feature, or any other material or method can be used to cover substrate 2402. Alternatively, if the nanotexturing is applied by electrochemical deposition, only the portion of substrate 2402 to which the nanofeatures are to be applied is dipped in a chemical bath so that only that part of substrate 2402 is coated.

Additionally, nanoparticles having different size ranges can be provided at surface 2404 to perform different functions. For example, a first particle size range is sized to enhance osteoconductivity and a second particle size range is sized to enhance anti-bacterial properties.

By way of example only, and referring back to FIG. 27, a texture extends over at least part of the exposed surface 2404. The texture comprises a plurality of nanofeatures, such as, for example, differing sizes and differing shapes, as described above. The nanofeatures inhibit bacterial growth on surface 2404 and can have a size range between about 0.01 nanometers and about 1,000 nanometers.

In an exemplary embodiment, a first range within the size range produces a first property and a second range within the size range produces a second property, different from the first property. For example, the first property can inhibit bacterial adhesion on the surface 2404 while the second property enhances osteointegration of the texture 2406. Further, the first size range can be between about 0.01 nanometers and about 1,000 nanometers, while the second size range can be between about 15 nanometers and about 3 millimeters.

Figure 28:
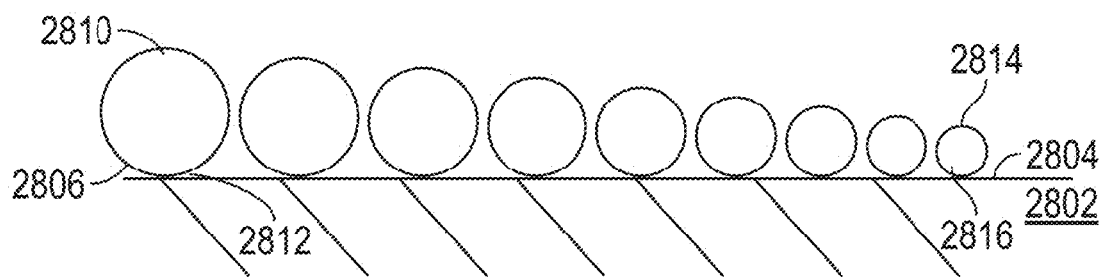
FIG. 28 shows a side elevational view of a treated substrate according to yet another exemplary embodiment of the present invention.

Referring to FIG. 28, a substrate 2802 has an exposed surface 2804 and has a texture 2806 over at least part of exposed surface 2804. Texture 2806 has a plurality of nanofeatures applied thereto. Texture 2806 has a first particle size 2810 at a first location 2812, a second particle size 2814 at a second location 2816, and a gradient 2818 of particle size from first particle size 2810 to second particle size 2814 between first location 2812 and second location 2816.

Figure 29:
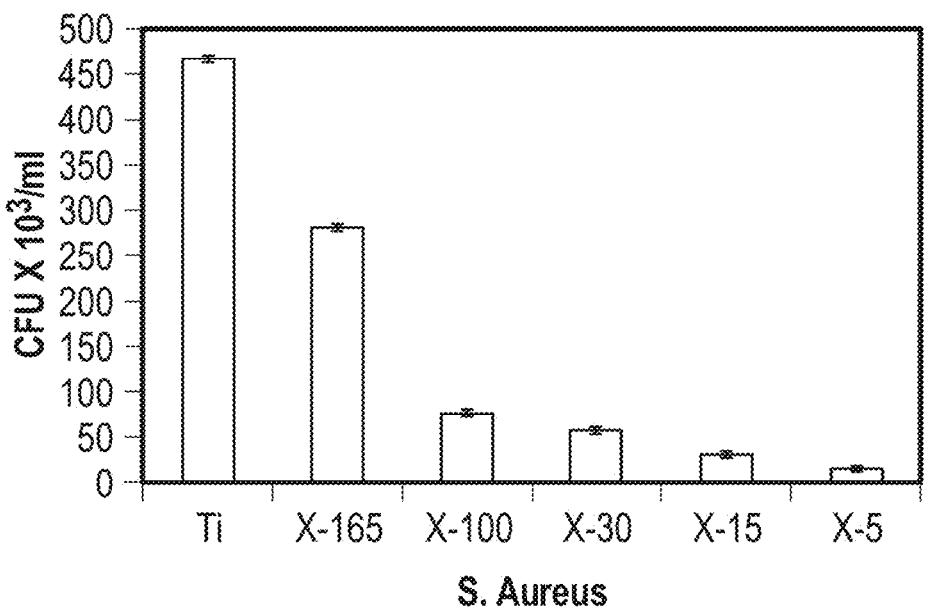
FIG. 29 shows a graph of different sized nanofeatures and their effect on *S. aureus* bacteria on a substrate.

FIG. 29 shows a graph of anti-bacterial properties of different sized nanofeatures and how they kill *S. aureus* bacteria. As seen on the graph, smaller sized nanofeatures (in the range of about 15 nanometers and smaller) are more effective at killing *S. aureus* than larger size nanofeatures (in the range of greater than about 30 nanometers).

Figure 30:
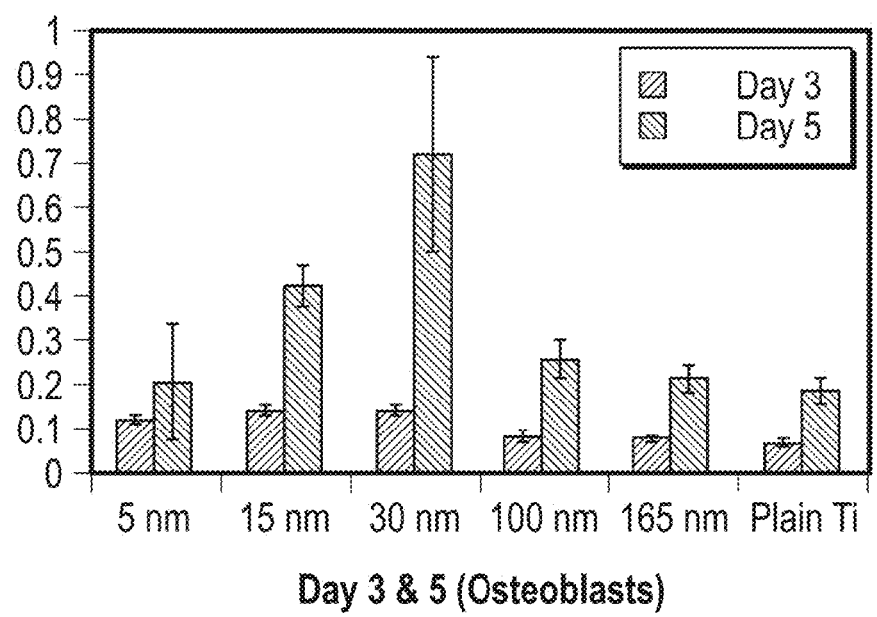
FIG. 30 shows a graph of the different sized nanofeatures and their effect on osteointegration capability on substrate

By comparison, FIG. 30 shows a graph of osteointegration of nanofeatures on a substrate after 3 days (left column of each pair) and 5 days (right column of each pair). As can be seen, nanofeatures in the 30 nanometer range demonstrate the largest amount of osteoblasts, indicating better osteointegration capability.

Therefore, by providing nanofeatures of differing size ranges, such as about 15 nanometers and smaller and about 30 nanometers, a nanotextured surface has both antimicrobial and osteointegration properties.

Figure 39:
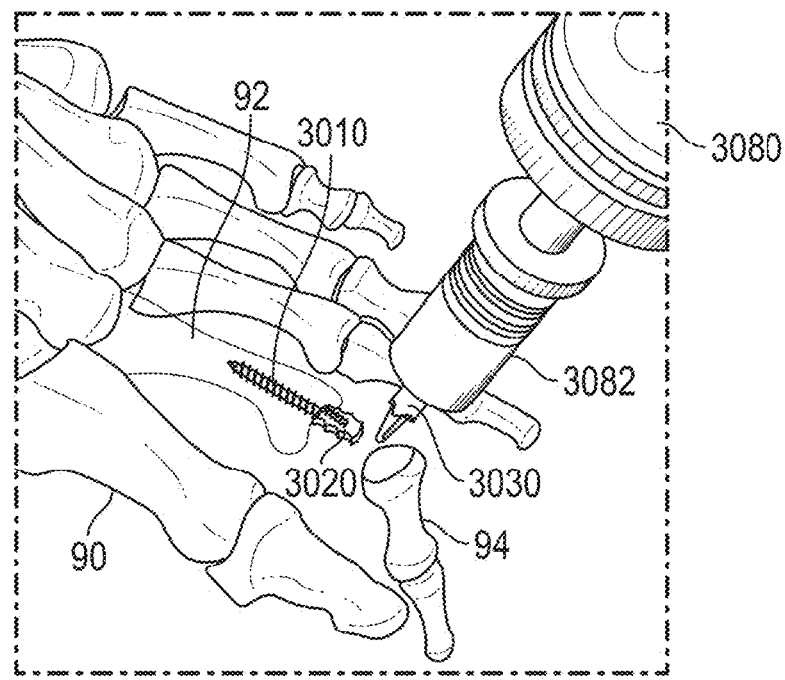
FIG. 39 is a perspective view of the driver assembly having been separated from the second implant portion.
Figure 40:
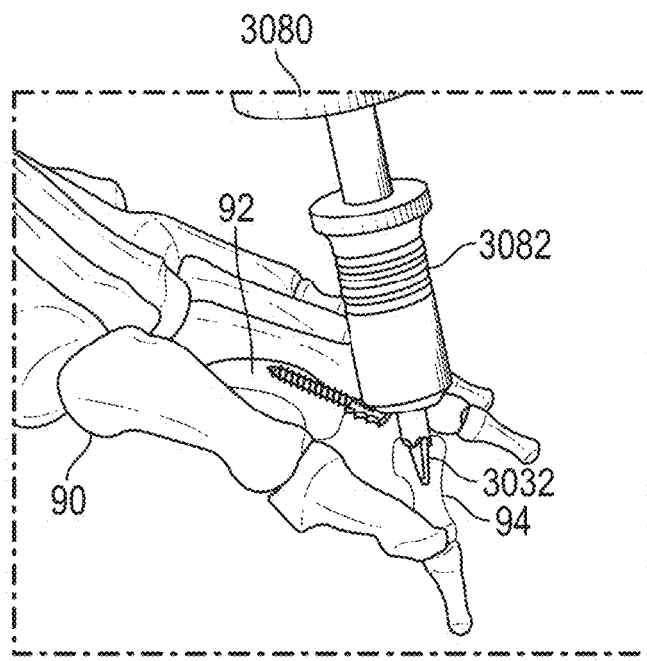
FIG. 40 is a perspective view of an opening being drilled in the second bone structure.
Figure 41:
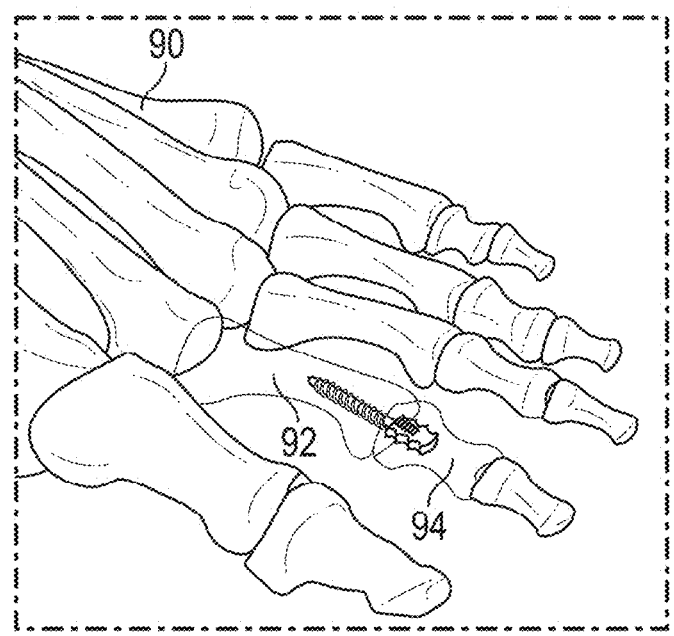
FIG. 41 is a perspective view of the second implant portion having been inserted into the second bone structure.
Figure 42:
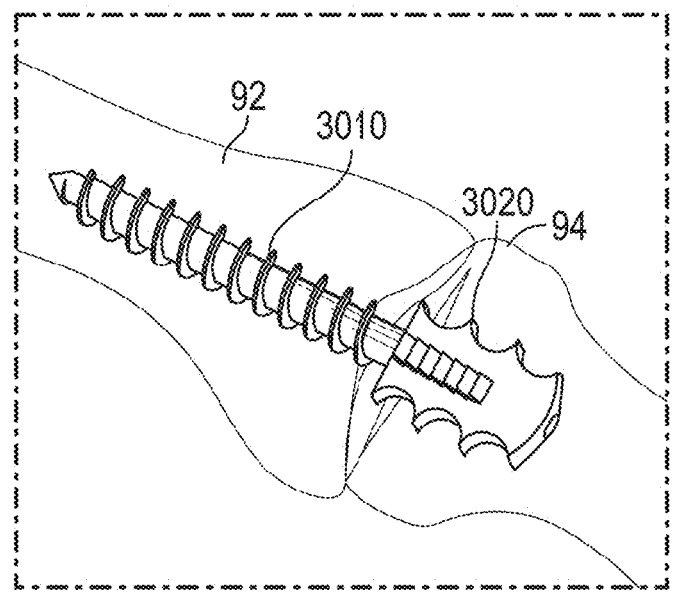
FIG. 42 is an enlarged view of the implant assembly inserted into both the first and second bone structures.

FIGS. 31-42 disclose a small joint fixation system 3000 ("system 3000") according to yet another alternative embodiment of the present invention. System 3000 can be used to fix a hammer toe condition by fixedly connecting a proximal phalangeal joint to a medial phalangeal joint as shown in FIGS. 41-42. Those skilled in the art, however, will recognize that system 3000 can be used to fixedly connect other joints, such as adjacent metacarpal joints of other joints, as well as to fixedly connect broken bone parts, such as, for example, two parts of a fibula, ulna, or other bone.

System 300 can be three-dimensionally printed to provide osteointegration and/or anti-microbial qualities, such as those described above. Additionally, nano-features can be incorporated into the three-dimensional printing. The different components of system 3000 can be constructed of similar or dissimilar materials, such as a particular metal and/or an oxide of the metal. Exemplary material from which system 3000 can be manufactured are titanium, PEEK or other suitable biocompatible material, and can be coated with a plasma spray.

System 3000 is a unitary construction medical device that comprises a first implant portion 3010 having a proximal end 3012, a second implant portion 3020 connected to first implant portion 3010. Second implant portion 3020 has a distal end 3022. An insertion tool, such as a driver assembly 3030, is removably connected to distal end 3022. Driver assembly 3030 comprises a drill 3032 connected to distal 3022 end at a connection 3034. Drill 3032 can be fluted to assist in digging out bone as drill 3032 is used to drill out bone matter.

As used with respect to system 3000 and as system 3000 is used to repair a hammer toe condition, the term "proximal" means a direction toward to the ankle and the term "distal" means a direction toward the tip of the toes of the foot into which system 3000 is being implanted.

First implant portion 3010 can be a helically threaded screw with one or more screw threads 3014. Proximal end 3012 can be a self-tapping tip. Alternatively, proximal end 3012 can require a pilot hole, depending on the size of the bone into which first implant portion 3010 is to be implanted. Optionally, first implant portion 3010 comprises a nano-textured surface 3016 between threads 3014.

Figure 32:
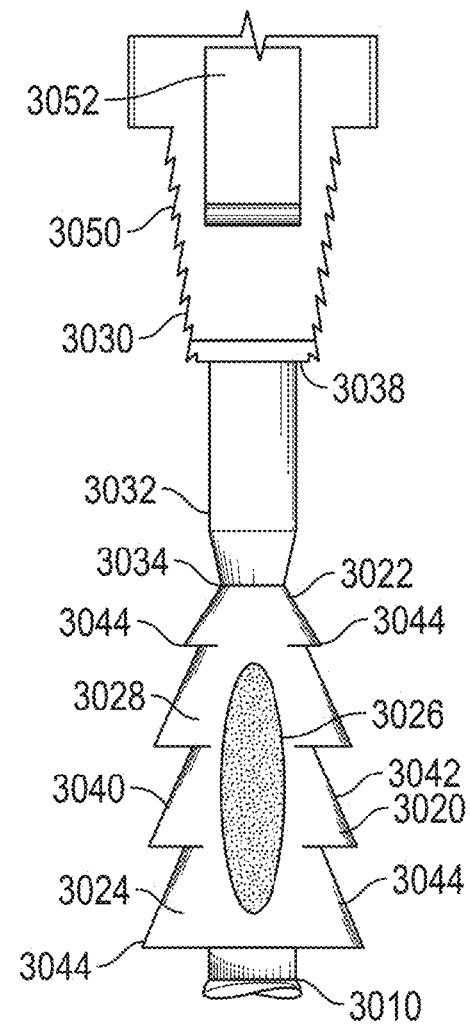
FIG. 32 is an enlarged view of the small joint implant encompassed by circle 32 in FIG. 31.
Figure 33:
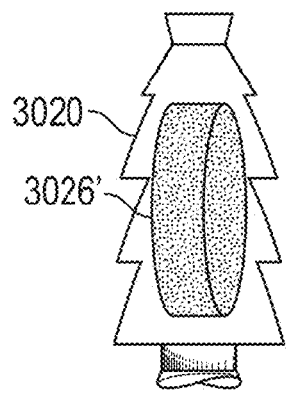
FIG. 33 is an enlarged view of an alternative embodiment of the small joint implant in FIG. 31.

Second implant portion 3020 is shown in detail in FIG. 32. Second implant portion 3020 includes a body portion 3024 having a lattice structure 3026. Lattice structure 3026 promotes osteointegration of second implant portion 3020 into the bone into which second implant portion 3020 is implanted. Additionally, lattice structure 3026 can be nano-textured with an anti-microbial coating to prevent the adhesion of microbes onto body portion 3024 and/or kill microbes that attach to body portion 3024. Lattice structure 3026 can be a generally oval shape as shown in FIG. 32, a generally oblong shape 3026', as shown in FIG. 33, or some other shape that provides a sufficiently large surface area without unduly impairing the structural integrity of second implant portion 3020.

Although not shown, instead of lattices 3026, 3026', body portion 3024 can be slotted or other configurations to promote osteointegration.

Referring back to FIG. 32, second implant portion 3020 can have a face 3028 having a generally planar profile. An opposing face (not shown) can also have a generally planar profile, parallel to face 3028. Sides 3040, 3042 each have a plurality of barbs 3044 extending outwardly therefrom to help secure second implant portion 3020 into bone. Alternatively, instead of second implant portion 3020 having parallel flat faces, second implant portion 3020 can have a generally cylindrical or other shape cross-section.

Figure 34:
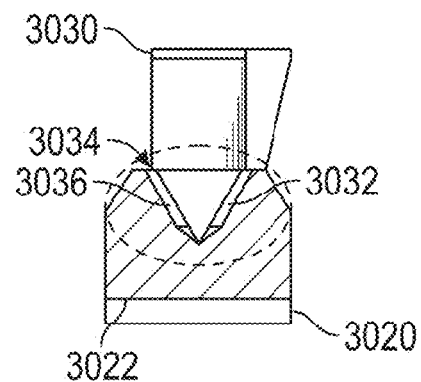
FIG. 34 is an enlarged view of the connection between an implant and a drill in the small joint implant shown in FIG. 31.
Figure 35:
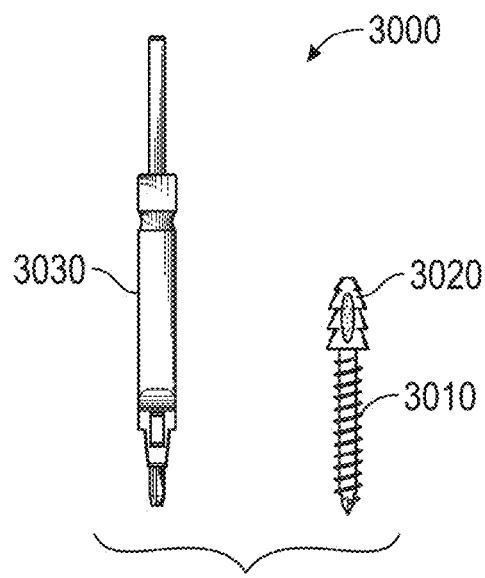
FIG. 35 is a front elevational view of the small joint implant shown in FIG. 31, having been separated.

Referring to FIG. 34, driver assembly 3030 includes a void 3036 in distal end 3022 of second implant portion 3020 adjacent to connection 3034. Void 3036 can be provided by manufacturing system 300 via three-dimensional printing, casting, or other suitable process that allows void 3032 to be formed inside distal end 3022 of second implant portion 3020. Void 3036 facilitates the separation of second implant portion 3020 from driver assembly 3030 after first implant portion 3010 is inserted into a bone, as shown in FIG. 35.

Further, first implant portion 3010 and second implant portion 3020 can be constructed from a first material and driver assembly 3030 can be constructed from a second material, different from the first material. By way of example only, the first material can be a polymer, such as, for example, PEEK, and the second material can be a metal, such as, for example, stainless steel or titanium.

Second implant portion 3020 can be overmolded onto driver assembly 3030 in the area of connection 3034. In separating driver assembly 3030 from second implant portion 3020, part of driver assembly 3030 (i.e., drill 3032) can be axially removed from second implant portion 3020.

Referring back to FIG. 32, driver assembly 3030 further comprises a face cutter 3038 distal of drill 3032. Face cutter 3038 is used to provide a flat bone surface at the proximal end of the bone into which second implant portion 3020 is to be implanted so that the bone can mate with the adjacent bone into which first implant portion 3010 is to be inserted.

A broach 3050 is located distal of face cutter 3038. Broach 3050 is used to shape and enlarge the opening formed by drill 3032 in the bone into which second implant portion 3020 is to be inserted.

Figure 36:
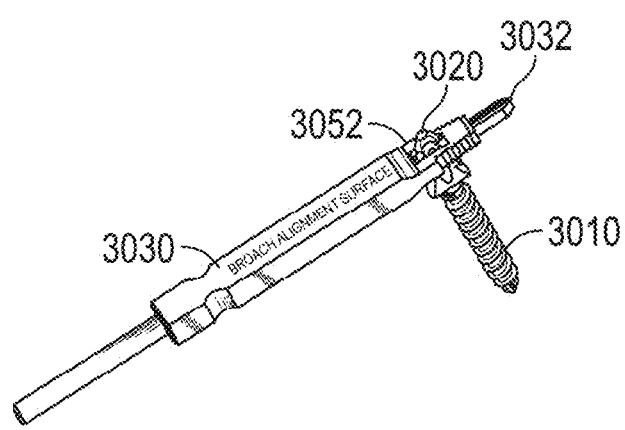
FIG. 36 is a perspective view of the small joint implant shown in FIG. 31, with a second implant portion inserted into a driver assembly.

Driver assembly 3030 also has a through-opening 3052 that is located distal of drill 3022. Through-opening 3052 is sized to allow second implant portion 3020 to be inserted thereinto after driver assembly 3030 is separated from second implant portion 3020, as shown in FIG. 36.

Figure 31:
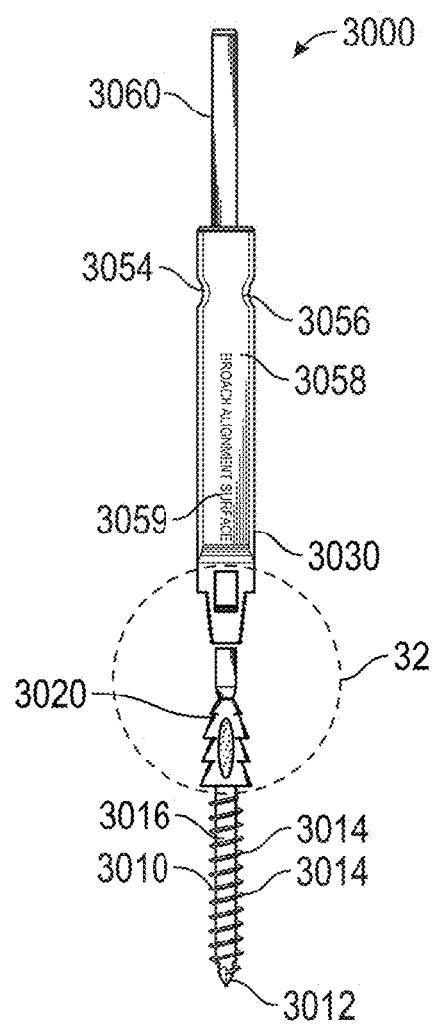
FIG. 31 is a front elevational view of a small joint implant according to an exemplary embodiment of the present invention.

As shown in FIG. 31, a circular groove 3054, 3056 is formed in driver assembly 3030, distal from through-opening 3052, that can used to secure driver assembly 303 into a chuck 3082 in a driver device 3080 (shown in FIG. 37) or other quick connection type handle.

Driver assembly 3030 has a generally flat face 3058 on which indicia 3059 is imprinted. Indicia 3059 can include lot numbers and/or other identifying information about system 3000. An opposing face (not shown) from face 3058 can also be flat.

Optionally, a wire driver 3060 extends distally from driver assembly 3030. Wire driver 3060 is a small diameter shank that can be utilized with a wire driver tool, as is known in the medical arts.

Referring to FIGS. 37-42, an exemplary method of joining adjacent bone structures 92, 94 in a foot 90 will now be discussed. Using system 3000, driver assembly 3030 is inserted into a chuck 3082 in a driver device 3080. In the absence of pre-drilling bone structure 92, proximal end 3012 of first implant portion 3010 is placed against first bone structure 92. While it is desired not to pre-drill bone structure 92 due to its size, it may be desirable to pre-drill a larger bone, such as, for example, a fibula or an ulna (not shown).

Figure 37:
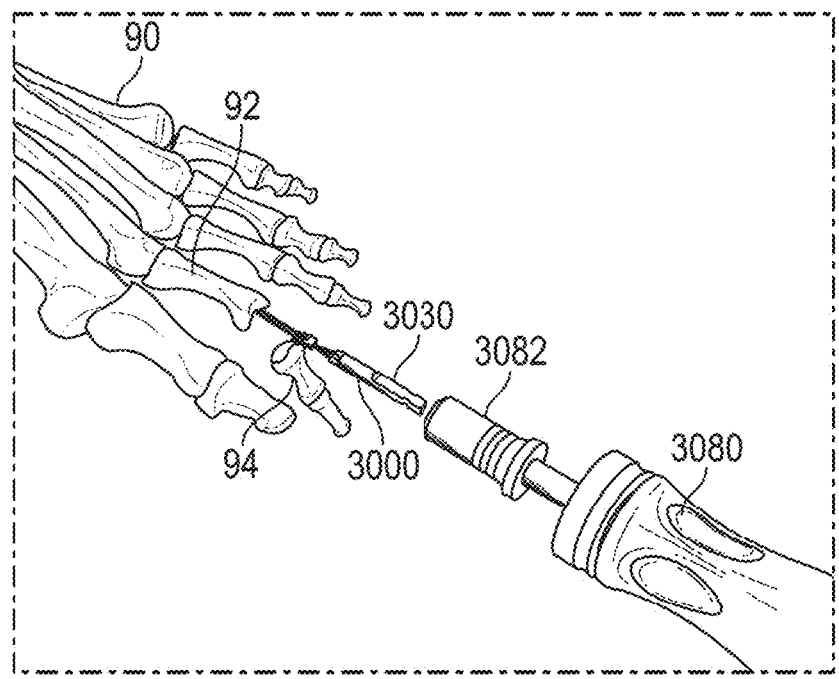
FIG. 37 is a perspective view of a first implant portion being inserted into a first bone structure.
Figure 38:
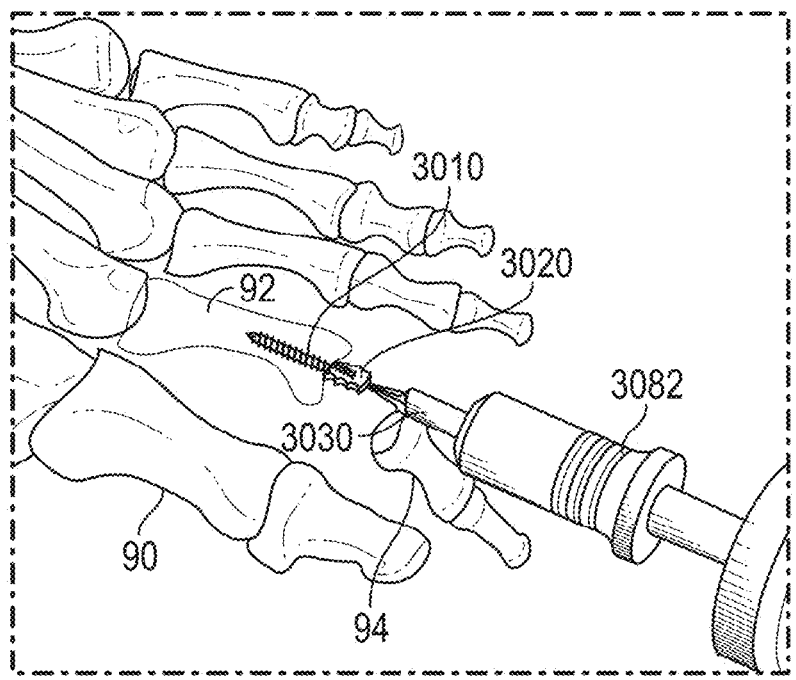
FIG. 38 is a perspective view of the first implant portion having been inserted into the first bone structure.

Driver device 3080 is then operated to rotate system 3000 and drill and insert first implant portion 3010 into first bone structure 92, as shown in FIGS. 37 and 38. Next, as shown in FIG. 39, second implant portion 3020 is separated from driver assembly 3030 by snapping distal end 3022 at connection 3034. Void 3036 assists in making a clean snap at void 3036. Optionally, inserting second implant portion 3020 can be inserted through through-opening 3052 in driver assembly 3030 and driver assembly 3030 is rotated to further screw first implant portion 3010 into bone structure 92.

Next, as shown in FIG. 40, drill 3032 is used to form an opening in second bone structure 94, adjacent to first bone structure 92. After the opening is made, face cutter 3038 is used to smooth second bone structure 94 to provide a smooth mating surface with first bone structure 92. If second implant portion 3020 is sufficiently larger than the opening formed in second bone structure 94, drill 3032 may be used multiple times to form multiple openings proximate to the originally formed opening, thereby forming a sufficiently large enough opening to insert second implant portion 3020. Broach 3050 can then be inserted into the enlarged opening and to smooth out its interior sides.

Figure 42A:
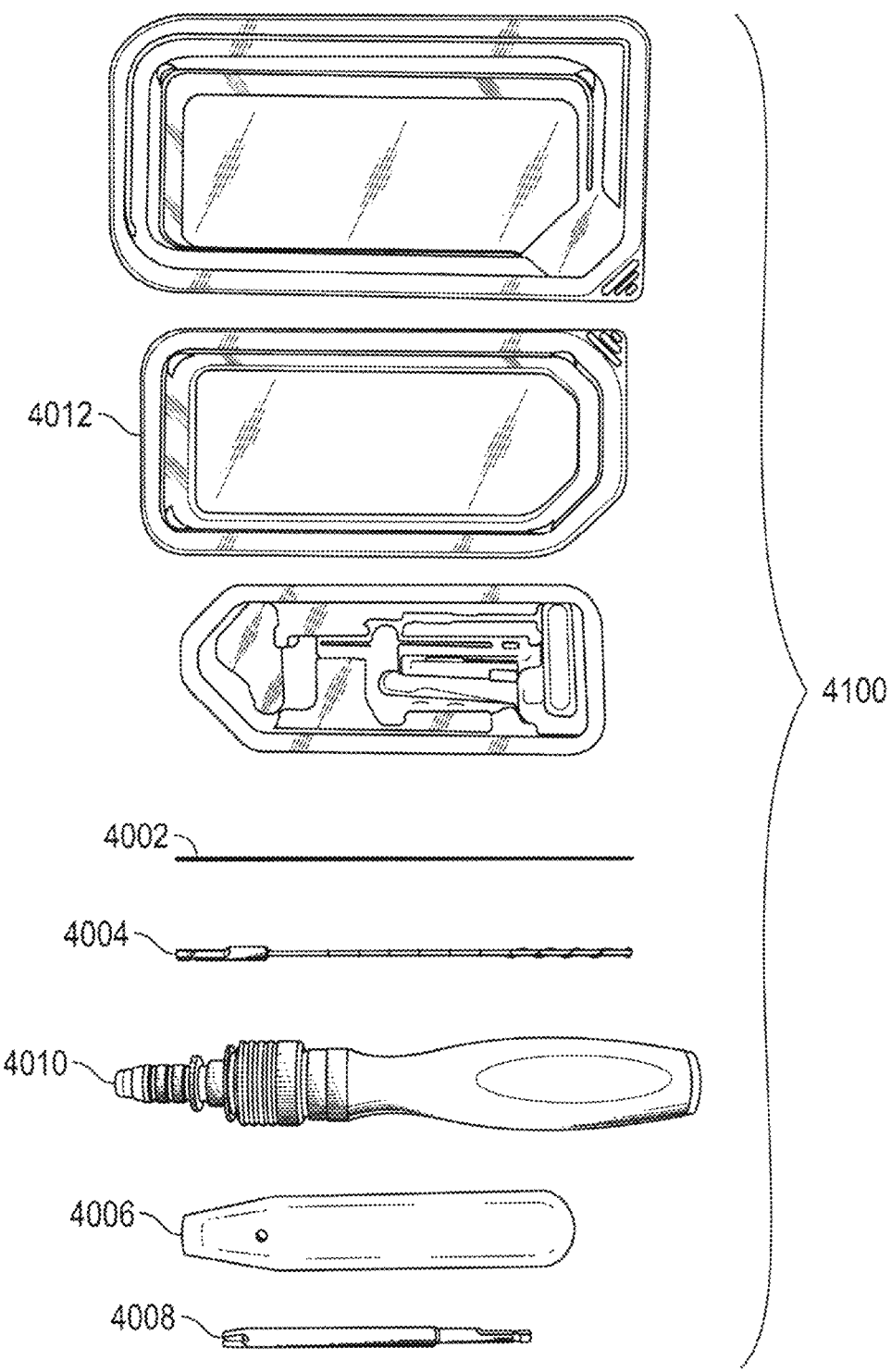
FIG. 42A is a top plan view of elements of a kit that can be used for implantation of the implant shown in FIG. 31.

After the opening in second bone structure 94 is prepared, as shown in FIGS. 41 and 42, second implant portion 3022 is inserted into the opening in second bone structure 94. Optionally, system 3000 can be provided as part of a kit 4000, as show in FIG. 42A. Kit 4000 can include other components used to implant system 3000 into bone, such as, for example, a scalpel with handle, one or more forceps, a retractor, a saw, a guide wire 4002, a drill 4004, an AO handle 4006, an countersink bit 4008, a driver (e.g., Torx®) 4010, as well as scissors, suture, a needle holder, an irrigation syringe, gauze, and other useful/necessary elements (not shown), packaged in sterile packaging 4012, to implant system 3000.

Figure 43:
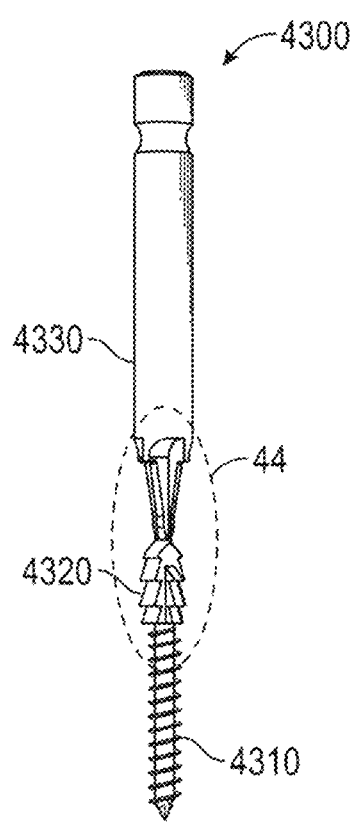
FIG. 43 is a perspective view of a small joint implant according to another exemplary embodiment of the present invention.
Figure 44:
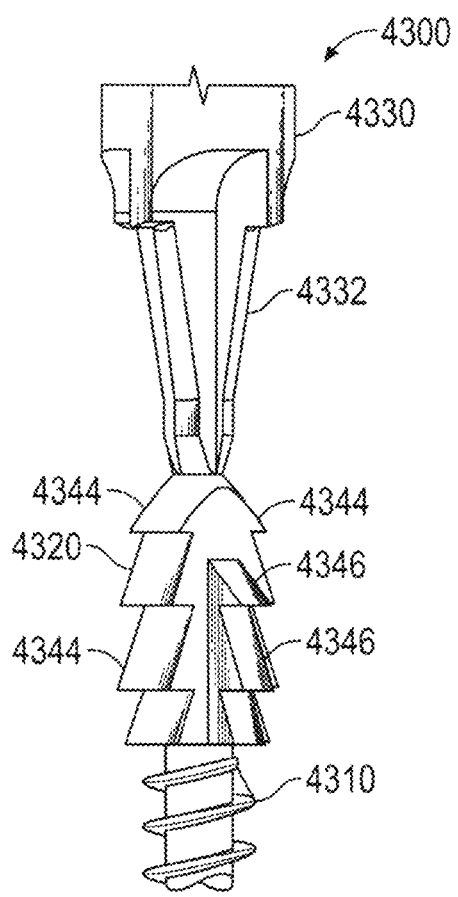
FIG. 44 is an enlarged perspective view of a connection between a drill and a second implant portion of the small joint implant shown in FIG. 43.

An alternative embodiment of a small joint fixation according to the present invention is an implant system 4300 is shown in FIGS. 43 and 44. System 4300 is similar to system 3000 except that second implant portion 4320 includes, in addition to a first set of barbs 4344 that are similar to barbs 3044 in system 3000 and extend in a first plane, a second set of barbs 4346 extends in a second plane, orthogonal to the first plane.

Additionally, instead of drill 3032, a fluted drill 4332 can be provided. Further, instead of axially pulling drill 3032 from second implant portion 3020, drill 4332 is snapped off from second implant portion 4320 at the tip of drill 4332.

Figures 45, 46:
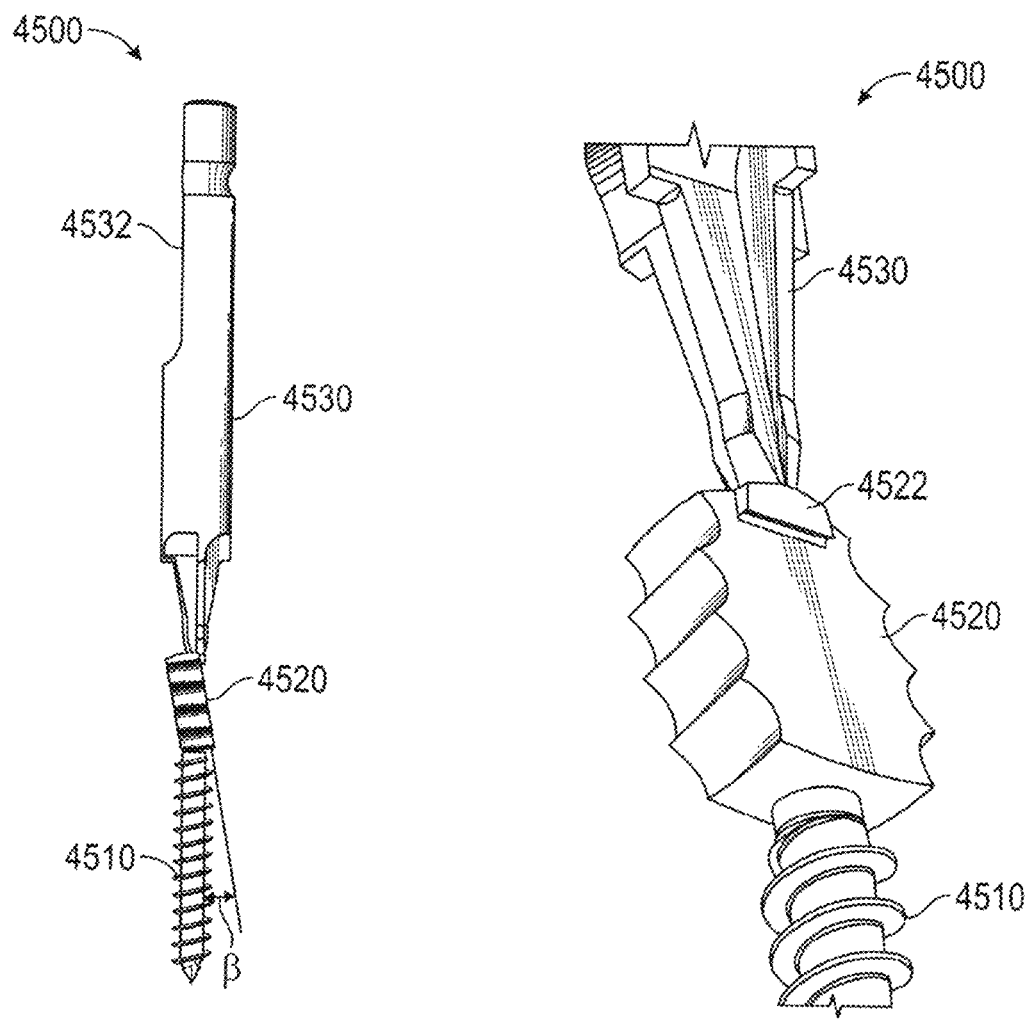
FIG. 45 is a perspective view of a small joint implant according to still another exemplary embodiment of the present invention.
FIG. 46 is an enlarged perspective view of a connection between a drill and a second implant portion of the small joint implant shown in FIG. 45.

Another alternative embodiment of a small joint fixation according to the present invention is an implant system 4500 is shown in FIGS. 45 and 46. System 4500 is similar to system 4300 except that second implant portion 4520 a angled at an angle β with respect to first implant portion 4510. In an exemplary embodiment, angle β is greater than zero degrees and less than about 20 degrees. In another exemplary embodiment, angle β is about 10 degrees.

Additionally, second implant portion 4520 includes a wedge 4522 that extends outwardly from a distal end of second implant portion 4520, proximate to driver assembly 4530. Wedge 4522 is used to retain second implant portion 4520 inside the opening in second bone portion 94.

Figure 47:
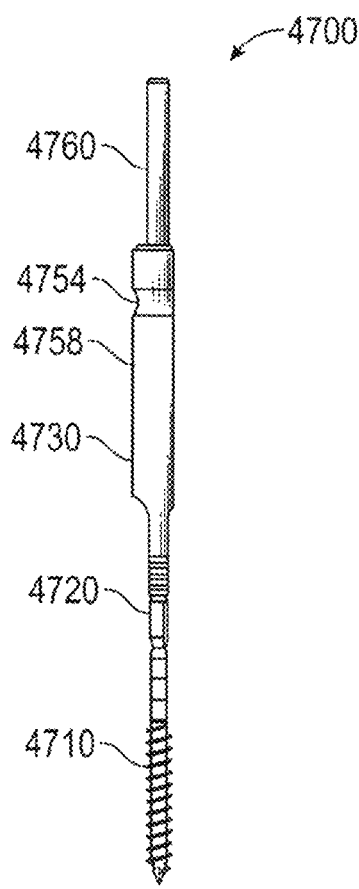
FIG. 47 is a side elevational view of a small joint implant according to another exemplary embodiment of the present invention.
Figure 48:
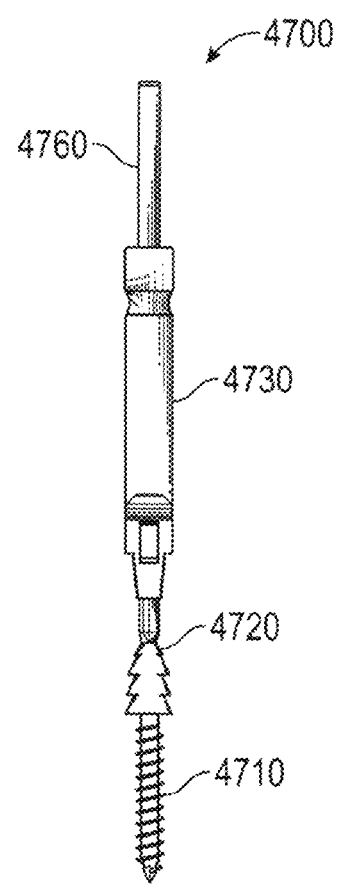
FIG. 48 is a front elevational view of the small joint implant shown in FIG. 47.

Another alternative embodiment of a small joint fixation according to the present invention is an implant system 4700 is shown in FIGS. 47 and 48. System 4700 is similar to system 3000 except that, instead of flat face 3058, driver assembly 4700 includes a generally semi-circular face 4758 and a semi-circular slot 4754.

Figure 49:
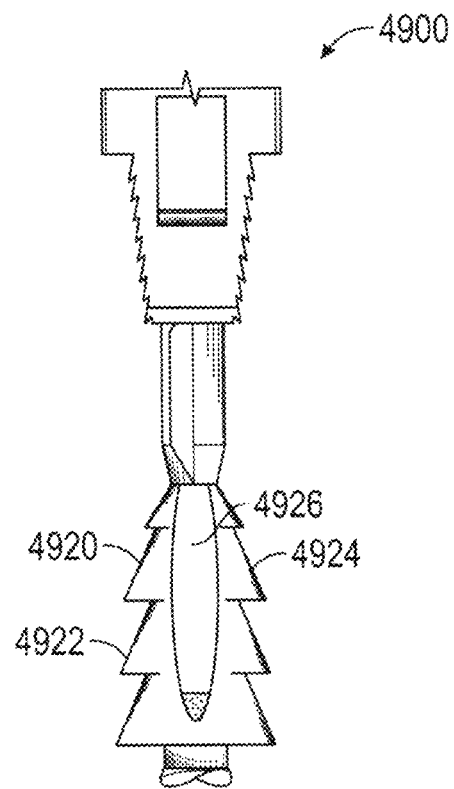
FIG. 49 is a front elevational view of a small joint implant according to another exemplary embodiment of the present invention.

Another alternative embodiment of a small joint fixation according to the present invention is an implant system 4900 is shown in FIG. 49. System 4800 is similar to system 3000 except that second implant portion 4920 comprises a first prong 4922, a second prong 4924, and a gap 4926 extending between first prong 4922 and second prong 4924. Gap 4926 can allow prongs 4922, 4924 to be spring loaded away from each other so that prongs 4922, 4924 are biased against the walls of the opening in second bone structure 94 after insertion into second bone structure 94.

Figure 50:
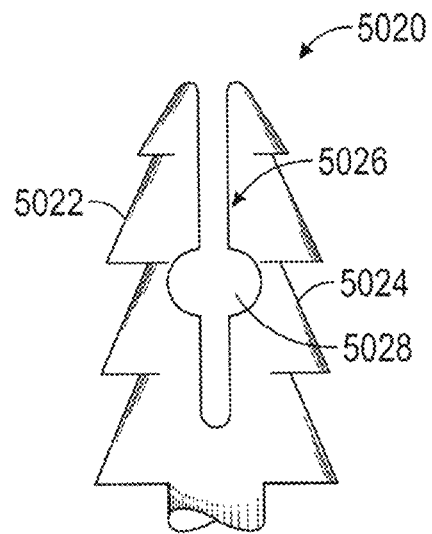
FIG. 50 is a front elevational view of a second implant portion of a small joint implant according to another exemplary embodiment of the present invention.

A second implant portion 5020 that can be used with any of the small joint fixation systems described herein is shown in FIG. 50. Second implant portion 5020 includes a first prong 5022, a second prong 5024, and a gap 5026 extending between first prong 5022 and second prong 5024. Similar to second implant portion 4920 described above, gap 5026 can allow prongs 5022, 5024 to be spring loaded away from each other so that prongs 5022, 5024 are biased against the walls of the opening in second bone structure 94 after insertion into second bone structure 94.

Gap 5026 in second implant portion 5020, however, also includes a generally circular hole 5028 that is large enough to allow the insertion of a tool (not shown) therein. The tool can have a tapered diameters such that, as the tool is inserted into hole 5028, prongs 5022, 5024 are forced apart from each other to expand second implant portion 5020 as second implant portion 5020 is being inserted into second bone structure 94.

Figure 51:
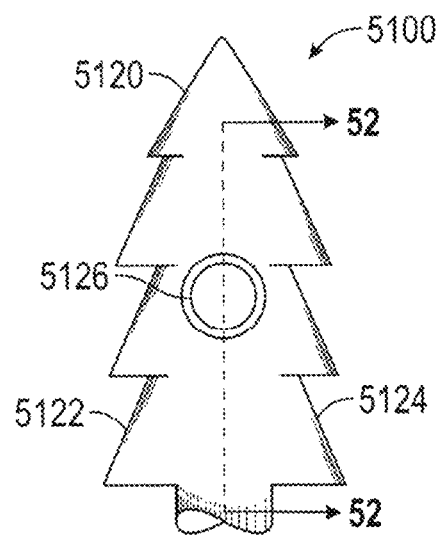
FIG. 51 is a front elevational view of a second implant portion of a small joint implant according to still another exemplary embodiment of the present invention.
Figure 52:
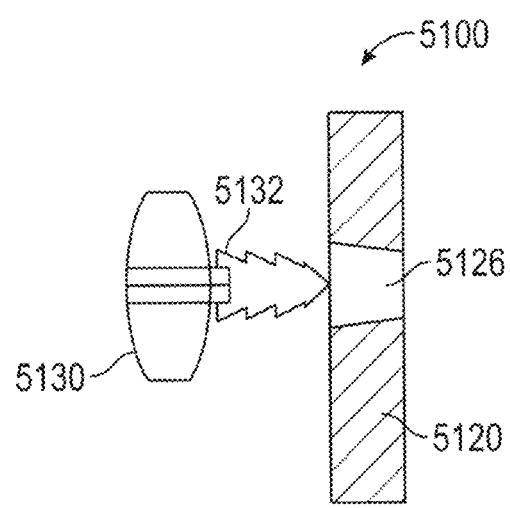
FIG. 52 is a sectional view of the second implant portion taken along lines 52-52 of FIG. 51.

A second implant portion 5120 that can be used with any of the small joint fixation systems described herein is shown in FIGS. 51 and 52. Second implant portion 5120 includes a tapered threaded through-opening 5126 extending between barbed sides 5122, 5124. A screw 5130 having threads 5132 can be inserted through second bone structure 54, and then into threaded through-opening 5126 to provide compression. Screw 5130 can be intentionally inserted off-center from opening 5126 to draw second implant portion 5120 toward screw 5130, thereby generating compression on second implant portion 5120.

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. An unitary construction medical device comprising:
    a first implant portion having a proximal end;
    a second implant portion connected to the first implant portion, the second implant portion having a distal end; and
    a driver assembly fixedly attached to and removably detachable from the distal end at a connection by snapping the driver assembly from the distal end at the connection, wherein the driver assembly comprises a drill connected to the distal end at the connection.

2. The unitary construction medical device according to claim 1, wherein the second implant portion comprises a body portion having a lattice structure.

3. The unitary construction medical device according to claim 1, comprising a void in the distal end adjacent to the connection.

4. The unitary construction medical device according to claim 1, wherein the driver assembly comprises a face cutter distal of the drill.

5. The unitary construction medical device according to claim 1, wherein the second implant portion comprises a first prong, a second prong, and a gap between the first prong and the second prong.

6. The unitary construction medical device according to claim 1, wherein the first implant portion comprises helical threads, and wherein the first implant portion further comprises a nano-textured surface between the threads.

7. The unitary construction medical device according to claim 1, wherein the second implant portion comprises a first set of barbs extending in a first plane and a second set of barbs extending in a second plane, orthogonal to the first plane.

8. The unitary construction medical device according to claim 1, further comprising a wire driver extending distally from the driver assembly.

9. An unitary construction medical device comprising:
    a first implant portion having a proximal end;
    a second implant portion connected to the first implant portion the second implant portion having a distal end; and
    a driver assembly fixedly attached to and removably detachable from the distal end at a connection by snapping the driver assembly from the distal end at the connection, wherein the driver assembly has a through-opening distal of a drill.

10. The unitary construction medical device according to claim 9, wherein the through-opening is sized to allow the second implant portion to be inserted thereinto.

11. A medical device comprising:
    a first implant portion;
    a second implant portion attached to the first implant portion; and
    a driver assembly having an instrument adapted to form an opening in bone, the driver assembly being integrally connected to and removably detachable from the second implant portion at a connection, distal from the first implant portion by snapping the driver assembly from the second implant portion at the connection, wherein the driver assembly comprises a drill at a proximal end thereof.

12. The medical device according to claim 11, wherein the driver assembly further comprises a broach.

13. The medical device according to claim 11, wherein the second implant portion comprises a void adjacent to the connection.

14. The medical device according to claim 11, wherein the driver assembly comprises a through-opening extending therethrough.

15. The medical device according to claim 11, wherein the driver assembly comprises a face cutter.

16. The medical device according to claim 11, wherein the second implant portion comprises a first prong, a second prong, and a gap between the first prong and the second prong.

* * * * *